(12) United States Patent
Kelly et al.

(10) Patent No.: US 11,307,892 B2
(45) Date of Patent: Apr. 19, 2022

(54) MACHINE-LEARNING FOR STATE DETERMINATION AND PREDICTION

(71) Applicant: Optum Services (Ireland) Limited, Dublin (IE)

(72) Inventors: Damian Kelly, Kildare (IE); Dominik Dahlem, Dublin (IE); Rick A. Hamilton, Charlottesville, VA (US)

(73) Assignee: Optum Services (Ireland) Limited, Dublin (IE)

( * ) Notice: Subject to any disclaimer, the term of this patent is extended or adjusted under 35 U.S.C. 154(b) by 895 days.

(21) Appl. No.: 16/020,206

(22) Filed: Jun. 27, 2018

(65) Prior Publication Data
US 2020/0004583 A1    Jan. 2, 2020

(51) Int. Cl.
| | |
|---|---|
| *G06F 9/48* | (2006.01) |
| *G06F 9/451* | (2018.01) |
| *G06N 20/00* | (2019.01) |
| *G06N 3/00* | (2006.01) |
| *G06N 7/00* | (2006.01) |
| *G16H 50/70* | (2018.01) |
| *G16H 20/10* | (2018.01) |
| *G16H 40/63* | (2018.01) |
| *G06F 17/00* | (2019.01) |

(52) U.S. Cl.
CPC ............ *G06F 9/4881* (2013.01); *G06F 9/451* (2018.02); *G06N 3/006* (2013.01); *G06N 7/005* (2013.01); *G06N 20/00* (2019.01); *G16H 20/10* (2018.01); *G16H 40/63* (2018.01); *G16H 50/70* (2018.01)

(58) Field of Classification Search
CPC ....... G06F 9/4881; G06F 9/451; G06N 3/006; G06N 7/005; G06N 20/00; G16H 50/70; G16H 20/10; G16H 40/63
See application file for complete search history.

(56) References Cited

U.S. PATENT DOCUMENTS

| | | | |
|---|---|---|---|
| 7,937,461 | B2 | 5/2011 | Kutzik et al. |
| 8,538,775 | B2 | 9/2013 | Skomra |
| 8,666,926 | B1 | 3/2014 | Nease et al. |
| (Continued) | | | |

FOREIGN PATENT DOCUMENTS

CN         102184312 B    7/2013

OTHER PUBLICATIONS

Samaneh et al., ("Thyme: Improving Smartphone Prompt Timing through Activity Awareness" Published 2017—16th IEEE International Conference on Machine Learning and Applications—pp. 315-322 (Year: 2017).*

(Continued)

*Primary Examiner* — Quoc A Tran
(74) *Attorney, Agent, or Firm* — Alston & Bird LLP

(57) ABSTRACT

Without timely reminders, certain individuals may be highly unlikely to complete various tasks scheduled for completion. For example, medicinal therapy regimen patients often have difficulty in remembering to take their prescribed medications in accordance with care provider specified instructions. By providing a reminder prompt generation system that utilizes machine-learning and/or artificial intelligence to determine appropriate reminder times and modalities for providing automated-prompting notifications to users, the users' adherence to scheduled task completions can be significantly increased.

27 Claims, 8 Drawing Sheets

(56) References Cited

U.S. PATENT DOCUMENTS

| | | |
|---|---|---|
| 9,361,772 B2 | 6/2016 | Johnson |
| 9,596,992 B2 | 3/2017 | Yang et al. |
| 9,679,113 B2 | 6/2017 | Hanina et al. |
| 9,808,404 B2 | 11/2017 | Nolan et al. |
| 2002/0083025 A1* | 6/2002 | Robarts .............. G06N 3/004 706/12 |
| 2006/0294563 A1 | 12/2006 | Guillorit |
| 2007/0008112 A1 | 1/2007 | Covannon et al. |
| 2007/0016443 A1 | 1/2007 | Wachman et al. |
| 2008/0030309 A1 | 2/2008 | Darrouzet |
| 2012/0173319 A1 | 7/2012 | Ferrara |
| 2015/0185713 A1 | 7/2015 | Glickfield et al. |
| 2015/0254427 A1 | 9/2015 | Burrows et al. |
| 2015/0310185 A1 | 10/2015 | Shah |
| 2016/0203290 A1 | 7/2016 | An et al. |
| 2016/0292373 A1 | 10/2016 | Spors et al. |
| 2016/0331643 A1 | 11/2016 | Chen et al. |
| 2017/0132391 A1 | 5/2017 | Morrison |
| 2019/0141919 A1* | 5/2019 | Kundra ............. G06K 9/00765 348/159 |

OTHER PUBLICATIONS

Aminikhanghahi Samaneh et al. "Thyme: Improving Smartphone Prompt Timing Through Activity Awareness," In 2017 16th IEEE International Conference on Machine Learning and Applications (ICMLA), Jan. 18, 2018, pp. 315-322. XP055612752. ISBN: 978-1-5386-1418-1. DOI: 10.1109/ICMLA.2017.0-141.

Fallahzadeh Ramin et al. "Demo Abstract: Mobile Sensing to Improve Medication Adherence," In 2017 16th ACM/IEEE International Conference on Information Processing in Sensor Networks (IPSN), Apr. 18, 2017, pp. 279-280, IEEE. XP058327603. ISBN: 978-1-4503-4590-4. DOI: 10.1145/3055031.3055045.

Feuz Kyle D. et al. "Automated Detection of Activity Transitions for Prompting," IEEE Transactions on Human-Machine Systems, vol. 45, No. 5, Nov. 6, 2014, pp. 575-585, IEEE, Piscataway, NJ, USA. XP011669384. ISSN: 2168-2291. DOI: 10.1109/THMS.2014.2362529.

International Searching Authority, International Search Report and Written Opinion for International Application No. PCT/US2019/035710, dated Sep. 2, 2019, (19 pages), The Netherlands.

Wu Qiong et al. "AI Empowered Context-Aware Smart System for Medication Adherence," International Journal of Crowd Science, vol. 1, No. 2, Jun. 12, 2017, pp. 102-109. XP055612497. ISSN: 2398-7294. DOI: 10.1108/IJCS-07-2017-0006.

Zanjal, Samier, V., et al., Medicine Reminder and Monitoring System for Secure Health Using IOT, Dec. 11, 2015, Procedia Computer Science, pp. 471-476, vol. 78, https://fardapaper.ir/mohavaha/uploads/2018/02/Fardapaper-Medicine-Reminder-and-Monitoring-System-for-Secure-Health-Using-IOT.pdf, Oct. 3, 2018.

Rao, Balachandra, et al., Medication Reminder and Monitoring System Using Iot, Jan. 1, 2017, ProQuest Database, pp. 80-84, vol. 4/issue 6, http://troindia.in/journal/ijcesr/vol4iss6part2/80-84.pdf, Oct. 3, 2018.

Nugent, Chns, et al., Can technology improve compliance to medicine? in 3rd International Conference on Smart Homes and Health Telematics—ICOST2005, Jul. 4, 2005, IOS Press, pp. 65-72, https://books.google.com/books?id=7AWMY0uz8awC&pg=PA72&lpg=PA72&dq=Can+technology+improve+compliance+to+medicine?+In+3rd+International+Conference+on+Smart+Homes+and+Health+Telematics+-+ICOST2005&source . . . .

Kelly, Damian, Minimal Infrastructure Radio Frequency Home Localisation Systems—PhD Thesis, Feb. 26, 2010, National University of Ireland, Maynooth Co. Kildare Ireland, 271 pages, http://citeseerx.ist.psu.edu/viewdoc/download:jsessionid=DF08DD9E2BE672599F247BB5238E7800?doi=10.1.1.467.8258&rep=rep1&type=pdf, Oct. 3, 2018.

Azimi, Iman, et al., Internet of Things for Remote Elderly Monitoring: A Study from User-Centered Perspective, Apr. 1, 2017, Journal of Ambient Intelligence and Humanized Computing, 22 pages, vol. 8/ issue 2, https://research.utu.fi/converis/getfile?id=18279618&portal=true, Oct. 3, 2018.

* cited by examiner

MACHINE-LEARNING FOR STATE DETERMINATION AND PREDICTION

BACKGROUND

According to various reports, a significant number of people with treatable ailments die each year because they do not take their medication(s) properly. Furthermore, a substantial percentage of hospital admissions can be associated with the effects of medicine non-compliance resulting in excessive healthcare costs. It is also expected that a percentage of nursing home admissions are due to medicine non-compliance. It is against this backdrop of poor adherence, and increased likelihood of preventable disease progression, increased hospitalizations which can significantly increase costs, that the present invention operates.

Various medication adherence programs exist which sense a patient's activity in his/her home environment and employ rules-based algorithms to decide when is the best time to remind them to take his/her medication. Such approaches are insufficient as they provide naïve prompts to the patient that do not understand the patient's likelihood to adhere in a given scenario. Such naïve prompts can be a nuisance and generally get ignored shortly after deployment, and are not effective to promote healthy activity such as medication adherence. There is, therefore, a need for systems and methods that consider various environmental and/or patient contexts that may be indicative of the likelihood of task adherence (e.g., medication or treatment adherence).

Applicant has identified a number of deficiencies and problems associated with conventional task adherence (e.g., medication adherence) systems. Through applied effort, ingenuity, and innovation, many of these identified problems have been solved by developing solutions that are included in embodiments of the present invention, many examples of which are described in detail herein.

BRIEF SUMMARY

In general, embodiments of the present invention provide methods, apparatus, systems, computing devices, computing entities, and/or the like for providing an optimal prompting model/strategy to maximize a user's medication adherence. Certain embodiments utilize machine-learning based models to train a prompting apparatus of most-effective notification strategies for users to maximize the likelihood that the user will take appropriate medication at appropriate times.

In accordance with one aspect, a method is provided. In one embodiment, the method comprises storing a schedule comprising a task to be performed by a user; providing a first automated-prompting notification to the user to perform the task; determining that the user completed the task responsive to the first automated-prompting notification, wherein (a) a first state of the user and a first state of the user's environment are stored in association with the first automated-prompting notification, (b) the first state of the user, the first state of the user's environment, and the first automated-prompting notification are used to train a prompting model/strategy and/or adherence model/prediction using machine learning, and (c) the prompting model/strategy and/or adherence model/prediction outputs one or more automated-prompting notifications; detecting a first input indicative of a context of an environment of the user; detecting a first input indicative of a context of the user; determining, based at least in part on the first input indicative of the context of the environment of the user and the first input indicative of the context of the user, a second state of the user and a second state of the user's environment; determining, based at least in part on the second state of the user, the second state of the user's environment, and the prompting model/strategy and/or adherence model/prediction, a second automated-prompting notification; and providing the second automated-prompting notification.

In accordance with another aspect, a computer program product is provided. The computer program product may comprise at least one computer-readable storage medium having computer-readable program code portions stored therein, the computer-readable program code portions comprising executable portions configured to store a schedule comprising a task to be performed by a user; provide a first automated-prompting notification to the user to perform the task; determine that the user completed the task responsive to the first automated-prompting notification, wherein (a) a first state of the user and a first state of the user's environment are stored in association with the first automated-prompting notification, (b) the first state of the user, the first state of the user's environment, and the first automated-prompting notification are used to train a prompting model/strategy and/or adherence model/prediction using machine learning, and (c) the prompting model/strategy and/or adherence model/prediction outputs one or more automated-prompting notifications; detect a first input indicative of a context of an environment of the user; detect a first input indicative of a context of the user; determine, based at least in part on the first input indicative of the context of the environment of the user and the first input indicative of the context of the user, a second state of the user and a second state of the user's environment; determine, based at least in part on the second state of the user, the second state of the user's environment, and the prompting model/strategy and/or adherence model/prediction, a second automated-prompting notification; and provide the second automated-prompting notification.

In accordance with yet another aspect, an apparatus comprising at least one processor and at least one memory including computer program code is provided. In one embodiment, the at least one memory and the computer program code may be configured to, with the processor, cause the apparatus to store a schedule comprising a task to be performed by a user; provide a first automated-prompting notification to the user to perform the task; determine that the user completed the task responsive to the first automated-prompting notification, wherein (a) a first state of the user and a first state of the user's environment are stored in association with the first automated-prompting notification, (b) the first state of the user, the first state of the user's environment, and the first automated-prompting notification are used to train a prompting model/strategy and/or adherence model/prediction using machine learning, and (c) the prompting model/strategy and/or adherence model/prediction outputs one or more automated-prompting notifications; detect a first input indicative of a context of an environment of the user; detect a first input indicative of a context of the user; determine, based at least in part on the first input indicative of the context of the environment of the user and the first input indicative of the context of the user, a second state of the user and a second state of the user's environment; determine, based at least in part on the second state of the user, the second state of the user's environment, and the prompting model/strategy and/or adherence model/prediction, a second automated-prompting notification; and provide the second automated-prompting notification.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION

Figure 1:
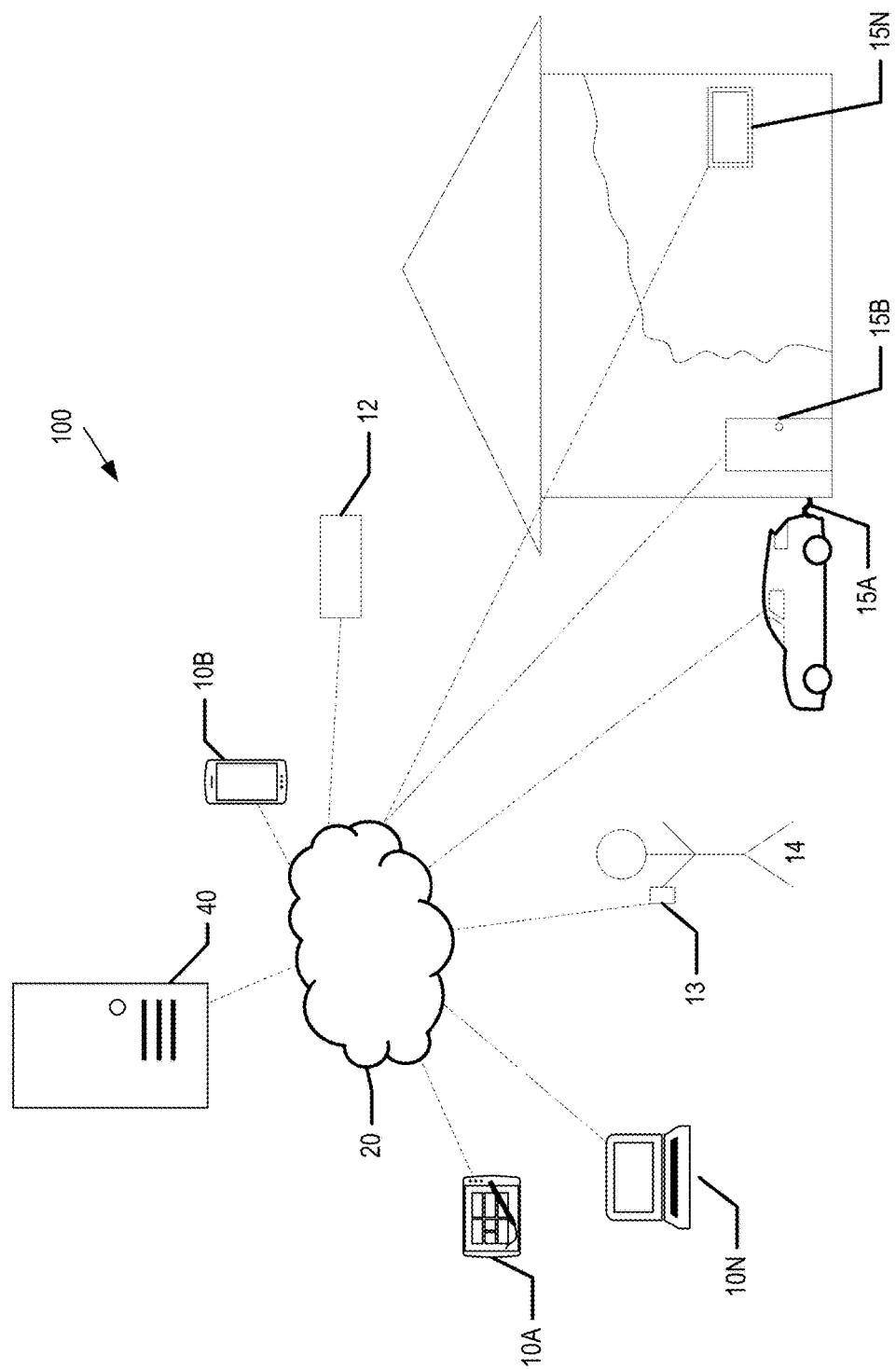
FIG. 1 is an exemplary overview of a system that can be used to practice embodiments of the present invention.

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout.

I. OVERVIEW

Discussed herein methods, apparatus, systems, computing devices, computing entities, and/or the like for a medication prompting artificial intelligence (MPAI) system for generating and/or transmitting prompts to various devices/entities associated with a user to provide reminders to take medications prescribed to the user according to a medicinal therapy regimen. As will be recognized, however, the disclosed concepts can be used to reminder a user to perform any type of task and are not limited to a particular context.

A. Technical Problem

Users (e.g., patients) respond differently to different prompts to remember to take medication, and various embodiments are configured to automatically determine user preferences (whether those preferences are conscious or subconscious) and to utilize those determined user preferences to provide automated-prompting notifications (e.g., reminder prompts) to those users in a manner to maximize the likelihood that the user will successfully take his/her medication.

For example, some people would prefer to be prompted immediately when they are finished with a task, such as eating. Other people might prefer to be prompted when they are participating in a task and ready to perform a quick diversion to take medication. Conversely, some people might prefer to be prompted when they are taking a prolonged break and have time to focus on taking medication. Aside from personal preferences, medical adherence prompting should also be provided as appropriate for people having deteriorating physical or mental states. For example, Alzheimer patients may exhibit a deterioration in speech or Parkinson patients may develop increased tremors. Although these medical conditions may not themselves lead to conscious user preferences regarding when a user should be prompted with a reminder to take prescribed medicines, these medical conditions may lead to changes in the likelihood that a particular user responds to medicinal reminder prompts at particular times and/or in relation to particular activities.

Because each user has different preferences; physical, mental, and/or medical characteristics; and environmental conditions in which he/she lives; generic prompting methodologies generated based on general population characteristics do not provide automated-prompting notifications (e.g., reminder prompts) at optimal intervals for individual users to maximize adherence to a prescribed medicinal treatment regimen. Moreover, they do not contemplate the various available modalities.

B. Technical Solution

Accordingly, various embodiments utilize machine learning models generated and/or trained based on user-specific activities and indications regarding whether a particular prompting model/strategy successfully resulted in the user taking his/her medication according to a prescribed medicinal therapy regimen. In certain embodiments, generic prompting models/strategies and/or adherence models/predictions (untrained or trained using an example data set) may be implemented via a MPAI system with an included prompting apparatus in communication with one or more devices associated with the user to provide prompts to a user to take medication at defined times. These prompts may be provided via any of a variety of user-accessible mechanisms in communication with the centralized prompting system, such as a mobile device carried by the user, an electronic device in the user's vicinity (e.g., a voice-activated personal assistant, a television, a visual personal assistant, and/or the like), and/or the like. The MPAI system may additionally collect sensor data from one or more sensors 15A-15N providing data indicative of user activity (e.g., via accelerometers within electronic devices, power sensors, building device sensors, and/or the like) and may correlate the collected data with success rates for prompts to the user to further train the prompting models/strategies and/or adherence models/predictions based on individual characteristics of a particular user. Thus, the MPAI system may train (e.g., continuously) the machine-learning model through reinforcement training to provide a prompting model/strategy that balances the likelihood of adherence (e.g., a predicted/modeled likelihood of adherence) to a prescribed medicinal therapy with prescribed timing requirements associated with the medicine. The machine-learning based prompting model/strategy and/or adherence model/prediction may be generated based at least in part on an interpretation of a determined current state of the user, a predicted future state of the user (e.g., based on current and/or scheduled activities), a current state of the user's environment, a predicted future state of the user's environment, and/or the like. The tracked states of the user may encompass activity states (e.g., as determined based on activity sensors), stress level (e.g., based at least in part on Galvanic Skin Response wearable sensors), conversation (e.g., via an ambient virtual personal assistant), and/or the like. Further, environmental state characteristics tracked by the system may encompass sensed presence of a user proximity to a particular environment (e.g., proximity of a wearable sensor to one or more other sensors within an environment, such as the user's medicine dispenser), and/or the like.

The prompting model/strategy and/or adherence model/prediction for a particular user may be further utilized to update general adherence models/predictions for various populations (e.g., these general models may be utilized to generate initial states of adherence models/predictions for further users). These populations may be based on user characteristics, medical conditions, and/or the like.

Moreover, the MPAI system may further be configured to provide a user and/or care providers associated with the user with information on the impact of his/her personal adherence to the prescribed medicinal therapy plan at optimally determined times to address potential issues of fatigue in medicinal adherence.

II. COMPUTER PROGRAM PRODUCTS, METHODS, AND COMPUTING ENTITIES

Embodiments of the present invention may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of an apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

III. EXEMPLARY SYSTEM ARCHITECTURE

FIG. 1 provides an illustration of an exemplary embodiment of the present invention. FIG. 1 shows system 100 including an example network architecture for a system, which may include one or more devices and sub-systems that are configured to implement some embodiments discussed herein. For example, the system 100 may include MPAI system 40, which can include, for example, a server or database, among other things (not shown). The MPAI system 40 may include any suitable network server and/or other type of processing device. In some embodiments, the MPAI system 40 may determine and transmit commands and instructions for training prompting models, generating optimal prompting strategies to maximize a user's medical adherence (e.g., a user's predicted medical adherence) to client devices 10A-10N using data stored via a sensing modalities database 300 (shown in FIG. 3) which may be stored as a part of and/or in communication with one or more client devices 10A-10N and/or the MPAI system 40. The sensing modalities database 300 includes information accessed and stored by the client device 10 to facilitate the operations of the prompting system (shown in FIG. 4).

MPAI system 40 can communicate with one or more client devices 10A-10N and/or other computing entities via communications network 20, and a plurality of client devices 10A-10N may communicate with one another and/or other computing entities via the network 20. In this regard, communications network 20 may include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, etc.). For example, communications network 20 may include a cellular telephone, an 802.11, 802.16, 802.20, and/or WiMax network. Further, the communications network 20 may include a public network, such as the Internet, a private network, such as an intranet, or combinations thereof, and may utilize a variety of networking protocols now available or later developed including, but not limited to TCP/IP based networking protocols. For instance, the networking protocol may be customized to suit the needs of the group-based communication interface. In some embodiments, the protocol is a custom protocol of JSON objects sent via a Websocket channel. In some embodiments, the protocol is JSON over RPC, JSON over REST/HTTP, and the like.

Client devices 10A-10N and/or MPAI system 40 may each be implemented as one or more computers, computing entities, desktop computers, mobile phones, tablets, phablets, notebooks, laptops, distributed systems, gaming consoles (e.g., Xbox, Play Station, Wii), watches, glasses, iBeacons, proximity beacons, key fobs, radio frequency identification (RFID) tags, ear pieces, scanners, televisions, dongles, cameras, wristbands, wearable items/devices, items/devices, vehicles, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. The depiction in FIG. 1 of "N" client devices is merely for illustration purposes. Any number of users and/or client devices 10 may be included in the system for accessing and/or implementing aspects of the MPAI system 40 and prompting system discussed herein (e.g., via one or more interfaces). In one embodiment, the client devices 10A-10N may be configured to display or provide a medication prompting interface on a display of the client device for viewing, creating, editing, and/or otherwise interacting with one or more automated-prompting notifications, which may be provided or pushed by the MPAI system 40 (and may be stored locally at one or more client devices 10A-10N). According to some embodiments, the MPAI system 40 may be configured to cause display or presentation of an interface for viewing, creating, editing, and/or otherwise interacting with one or more automated-prompting notifications.

As indicated above, the client devices 10A-10N may be any computing device as defined above. Electronic data received by the MPAI system 40 from the client devices 10A-10N may be provided in various forms and via various methods. For example, the client devices 10A-10N may include desktop computers, laptop computers, smartphones, netbooks, tablet computers, wearables, and the like. In embodiments where a client device 10A-10N is a mobile device, such as a smart phone or tablet, the client device 10A-10N may execute an "app" such as the medical adherence prompting application to interact with the MPAI system 40. Such apps are typically designed to execute on mobile devices, such as tablets or smartphones. For example, an app may be provided that executes on mobile device operating systems such as iOS®, Android®, or Windows®. These platforms typically provide frameworks that allow apps to communicate with one another and with particular hardware and software components of mobile devices. For example, the mobile operating systems named above each provide frameworks for interacting with location services circuitry, wired and wireless network interfaces, user contacts, and other applications. Communication with hardware and software modules executing outside of the app is typically provided via application programming interfaces (APIs) provided by the mobile device operating system.

Additionally or alternatively, the client device 10A-10N may interact with the MPAI system 40 via a web browser. As yet another example, the client device 10A-10N may include various hardware or firmware designed to interface with the MPAI system 40.

As also shown in FIG. 1, a plurality of sensors 15A-15N (which in certain embodiments may be a part of one or more client devices 10A-10N) provide information to the MPAI system 40 (e.g., via network 20). For example, the sensors 15A-15N may comprise door open/close sensors, drawer open/close sensors, medication container sensors, weight sensors, motion sensors, power sensors for various devices (e.g., a television, a stereo, a video game console, one or more lights, one or more fans, a stove, a treadmill, an exercise bicycle, and/or the like), flow meters for various devices (e.g., a faucet flow meter, a water heater flow meter, a natural gas flow meter (e.g., at a gas-stove burner), and/or the like, proximity sensors (e.g., Bluetooth sensors, near field communication (NFC) sensors), voice-activated sensors (e.g., voice activated personal digital assistants), electric-car charging sensors, and/or the like. It should be understood that these sensors, as well as other sensors discussed herein, are provided merely as examples, and any sensors that may be indicative of the location and/or activity of a user may be provided.

In some embodiments, the MPAI system 40 may be configured to be in communication with the one or more client devices 10A-10N to establish a cloud-based, device-based, and/or or fog-based (e.g., a networked system within a home, building, business, and/or the like, edge device, fog device or full public cloud) prompting system for a user. Moreover, the MPAI system 40 may further offer a hybrid architecture to enable opt-in community-based feedback, transfer learning of disease-specific medical prompting strategies, and dietary and activity-based recommendations. The plurality of sensors 15A-15N may be embodied by Internet of Things (IoT) devices. In certain embodiments, a system 100 as illustrated in FIG. 1 may further include an optional medication tracker/dispenser 12b which may provide information as to whether the user 14 took his or her medication. In some example embodiments, one or more ambient/personal computing devices 13b (portable and/or wearable computing devices which may themselves constitute one type of client device 10) may also provide context information that may be utilized by the prompting system. The one or more ambient/personal computing devices may comprise motion sensors, home activity sensors, phone accelerometers, phone Wi-Fi readings etc. As depicted in FIG. 1, user 14 may interact with any of the client devices 10A-10N, sensors 15A-15N, and/or other devices 12-13 which in turn provide information to the MPAI system 40, or other computing entities storing data for generating and/or implementing an optimal prompting model/strategy to maximize a user's medical adherence.

A. Exemplary Client Device

Figure 2:
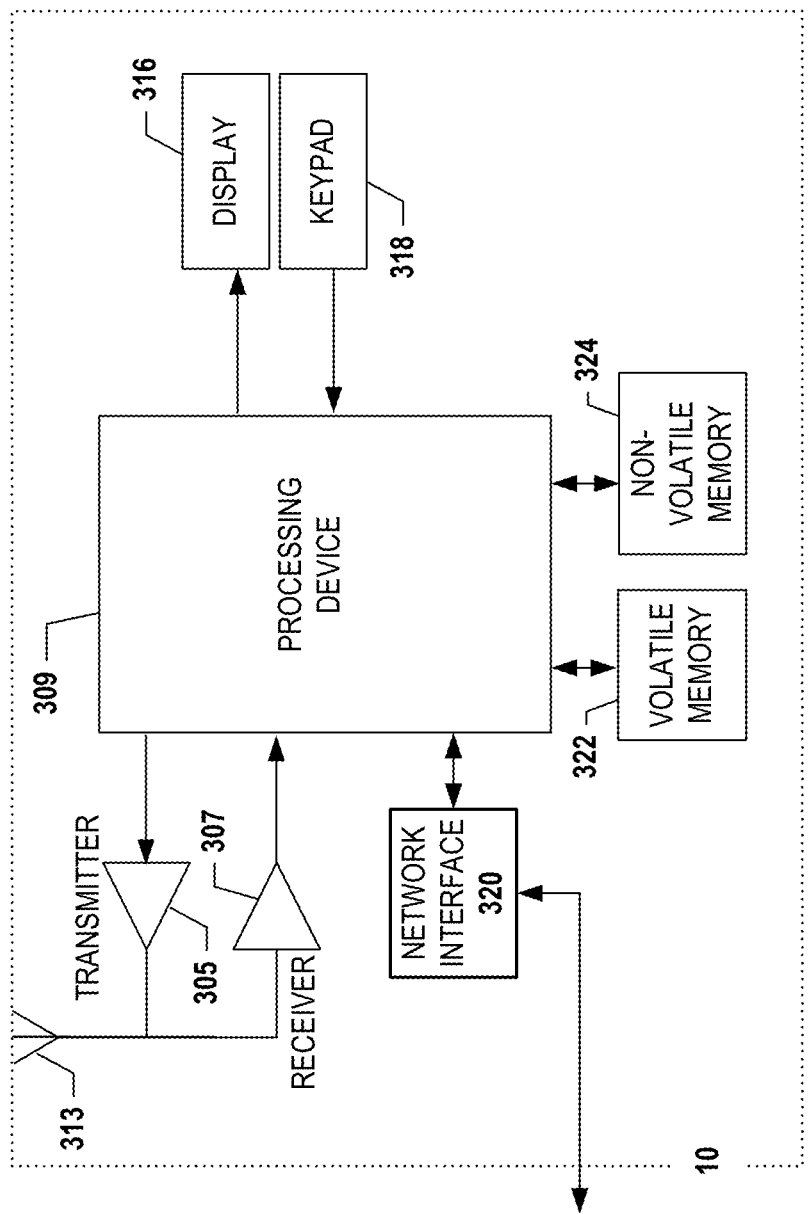
FIG. 2 illustrates an example client device in accordance with some embodiments discussed herein.

FIG. 2 provides an illustrative schematic representative of client device 10A-10N that can be used in conjunction with embodiments of the present invention. As shown in FIG. 2, a client device 10 can include an antenna 313, a transmitter 305 (e.g., radio), a receiver 307 (e.g., radio), and a processing element 309 that provides signals to and receives signals from the transmitter 305 and receiver 307, respectively. The signals provided to and received from the transmitter 305 and the receiver 307, respectively, may include signaling information/data in accordance with an air interface standard of applicable wireless systems to communicate with various entities, such as a MPAI system 40, another client device 10, and/or the like. In this regard, the client device 10 may be capable of operating with one or more air interface standards, communication protocols, modulation types, and access types. More particularly, the client device 10 may operate in accordance with any of a number of wireless communication standards and protocols. In a particular embodiment, the client device 10 may operate in accordance with multiple wireless communication standards and protocols, such as GPRS, UMTS, CDMA2000, 1×RTT, WCDMA, TD-SCDMA, LTE, E-UTRAN, EVDO, HSPA, HSDPA, Wi-Fi, WiMAX, UWB, IR protocols, Bluetooth protocols, USB protocols, and/or any other wireless protocol.

Via these communication standards and protocols, the client device 10 can communicate with various other entities using concepts such as Unstructured Supplementary Service information/data (USSD), Short Message Service (SMS), Multimedia Messaging Service (MMS), Dual-Tone Multi-Frequency Signaling (DTMF), and/or Subscriber Identity Module Dialer (SIM dialer). The client device 10 can also download changes, add-ons, and updates, for instance, to its firmware, software (e.g., including executable instructions, applications, program modules), and operating system.

According to one embodiment, the client device 10 may include location determining aspects, devices, modules, functionalities, and/or similar words used herein interchangeably. For example, the client device 10 may include outdoor positioning aspects, such as a location module adapted to acquire, for example, latitude, longitude, altitude, geocode, course, direction, heading, speed, UTC, date, and/or various other information/data. In one embodiment, the location module can acquire data, sometimes known as ephemeris data, by identifying the number of satellites in view and the relative positions of those satellites. The satellites may be a variety of different satellites, including LEO satellite systems, DOD satellite systems, the European Union Galileo positioning systems, the Chinese Compass navigation systems, Indian Regional Navigational satellite systems, and/or the like. Alternatively, the location information/data may be determined by triangulating the computing entity's position in connection with a variety of other systems, including cellular towers, Wi-Fi access points, and/or the like. Similarly, the client device 10 may include indoor positioning aspects, such as a location module adapted to acquire, for example, latitude, longitude, altitude, geocode, course, direction, heading, speed, time, date, and/or various other information/data. Some of the indoor aspects may use various position or location technologies including RFID tags, indoor beacons or transmitters, Wi-Fi access points, cellular towers, nearby computing devices (e.g., smartphones, laptops) and/or the like. For instance, such technologies may include iBeacons, Gimbal proximity beacons, BLE transmitters, NFC transmitters, and/or the like. These indoor positioning aspects can be used in a variety of settings to determine the location of someone or something to within inches or centimeters.

The client device 10 may also comprise a user interface device comprising one or more user input/output interfaces (e.g., a display 316 and/or speaker/speaker driver coupled to a processing element 309 and a touch screen, keyboard, mouse, and/or microphone coupled to a processing element 309). For example, the user output interface may be configured to provide an application, browser, user interface, dashboard, webpage, and/or similar words used herein interchangeably executing on and/or accessible via the client device 10 to cause display or audible presentation of information/data and for user interaction therewith via one or more user input interfaces. As just one specific example, the client device 10 may be configured to output various interface screens associated with a medication prompting application, which may provide various setup/registration screens and/or may provide one or more reminder prompts for a user of the client device. The user input interface can comprise any of a number of devices allowing the client device 10 to receive data, such as a keypad 318 (hard or soft), a touch display, voice/speech or motion interfaces, scanners, readers, or other input device. In embodiments including a keypad 318, the keypad 318 can include (or cause display of) the conventional numeric (0-9) and related keys (#, *), and other keys used for operating the client device 10 and may include a full set of alphabetic keys or set of keys that may be activated to provide a full set of alphanumeric keys. In addition to providing input, the user input interface can be used, for example, to activate or deactivate certain functions, such as screen savers and/or sleep modes. Through such inputs the client device 10 can collect information/data, user interaction/input, and/or the like.

The client device 10 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, RRAM, SONOS, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, VRAM, cache memory, register memory, and/or the like. The volatile and non-volatile storage or memory can store databases, database instances, database management system entities, data, applications, programs, program modules, scripts, source code, object code, byte code, compiled code, interpreted code, machine code, executable instructions, and/or the like to implement the functions of the client device 10. Again, as a specific example, the client device memory storage areas (encompassing one or both of the volatile memory 322 and/or non-volatile memory 324) may store the medication prompting application thereon, which itself may encompass a prompting model/strategy and/or an adherence model/prediction trained for providing optimal medical prompts to the user via one or more artificial intelligence and/or machine-learning algorithms. As discussed herein, the prompting model/strategy to be implemented with a particular user is indicative of when particular prompts are to be provided to the user. The prompting model/strategy may define fixed time intervals for providing prompts to the user, trigger events that may be detected prior to providing a particular prompt, and/or the like. Moreover, as discussed herein, the prompting model/strategy may change over time based on the results of the various machine-learning configurations as discussed herein. As one aspect that may be considered by those machine-learning configurations when determining an appropriate prompting model/strategy for a user, an adherence model/prediction may be utilized to determine a predicted likelihood that the user will adhere to a prescribed program (e.g., medication program) according to a predicted future state of the user. Similar to the prompting model/strategy, the adherence model/prediction may be embodied as an artificial intelligence system (or portion of a system) taught via machine learning to provide data indicative of a predicted likelihood that the user will adhere to the prescribed program during a period of time that the user is in a particular state, at some time in the future. In certain embodiments, training the prompting model/strategy may be based at least in part on the adherence model/prediction results (including the predicted likelihood of adherence for a user while the user is in some future state) for a particular user. The memory storage areas discussed herein may further encompass one or more aspects of a sensing modalities database 300, as discussed in greater detail herein (however the sensing modalities database 300 may be stored in association with the MPAI system 40 in certain embodiments). As discussed herein, the medication prompting application may be associated with and/or provided by an organization engaged in healthcare-related services, via the MPAI system 40.

In one embodiment, the client devices 10 may be configured to (independently and/or jointly with other client devices 10A-10N in the communication network 20) operate as prompting apparatuses configured to provide reminder prompts to the user at determined optimal times, and via determined optimal prompting modalities. The client devices 10A-10N may therefore store a medication prompting application or be in communication with one.

In some example embodiments, a sensing modalities database 300 and/or MPAI system 40 may be in communication with the one or more client devices 10A-10N and may be configured to perform the functionality discussed herein related to storing, generating, and/or modeling a prompting model/strategy to maximize a user's medical adherence. In some embodiments, some or all of the functionality of storing, generating, and/or modeling a prompting model/strategy may be performed by processing device 309. In this regard, the example processes and algorithms discussed herein can be performed by at least one processing device 309, sensing modalities database 300, and/or MPAI system 40.

B. Exemplary Sensing Modalities Database

Figure 3:
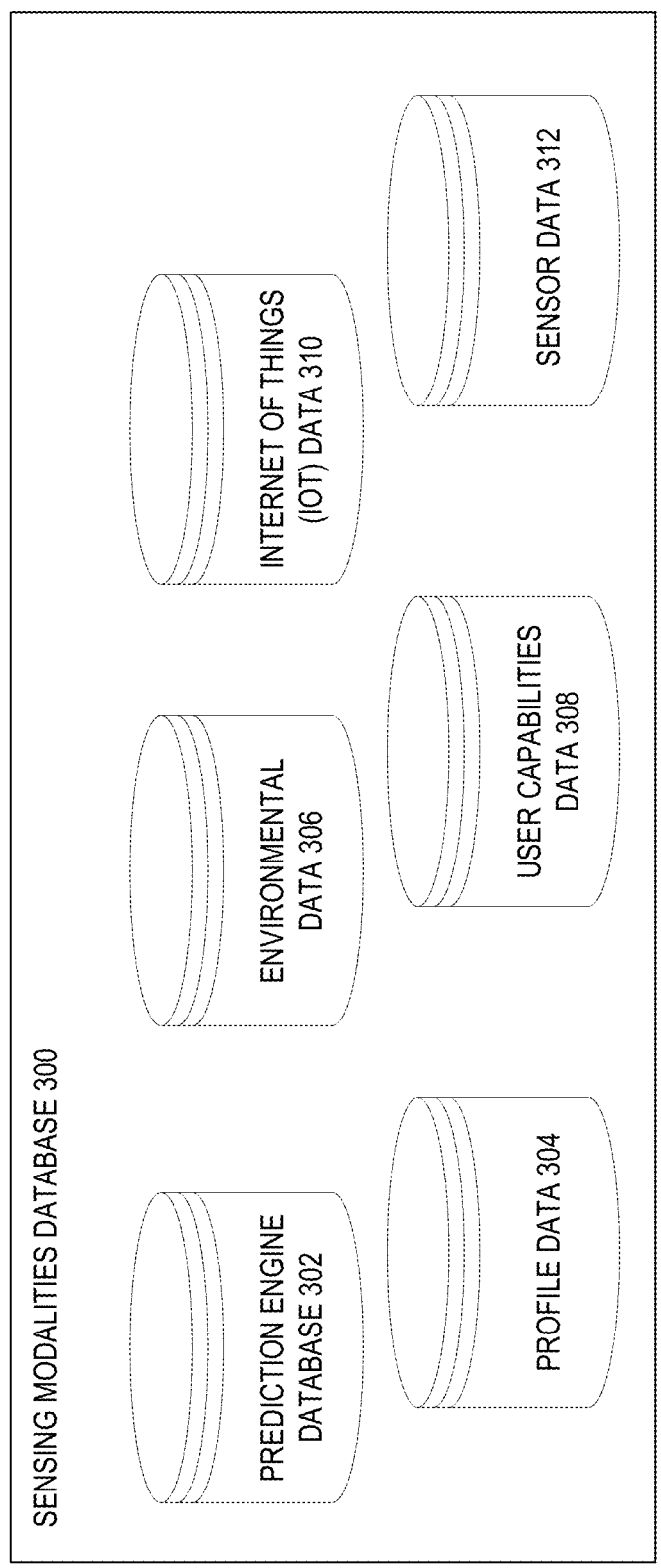
FIG. 3 illustrates an example sensing modalities database in accordance with some embodiments discussed herein.

In some embodiments, a sensing modalities database 300 may be provided that includes a prediction engine database 302, profile data 304, environmental data 306, user capabilities data 308, IoT data 310, and/or sensor data 312 as depicted in FIG. 3. As discussed herein, the sensing modalities database 300 may be provided within memory associated with one or more client devices 10A-10N and/or the MPAI system 40.

Profile data 304, in some embodiments, may include medical data, ideal medicinal schedule, biographical data and/or preference data associated with individual users or groups of users. Environmental data 306 may include anything that can be measured or captured in an environment and/or indicative of the context of the environment, such as a level of illumination, a level and spectrum of background noises, an activation state of a device within the environment (e.g., TV, audio streaming device, heating state from connected thermostat, motion from third party home automation systems, power sensing level from whole-home power sensors or individual plug socket power sensing devices), and/or a user's proximity to an object or device.

User capabilities data 308 may include various information related to a trained set of user capabilities the MPAI system 40 knows the user possesses in a given environment and/or indicative of the context of the user, such as a movement of the user, an activity of the user, an action of the user, a gesticulation of the user, a vocal expression of the user, a facial expression of the user, a schedule of the user, a visual perception of the user, an auditory perception of the user, a tactile perception of the user, a cognitive load of the user, a social restriction of the user, an interaction of the user with a device, and interaction of the user with other users, an interaction of the user with a medical dispenser, an interaction of the user with services, and an inferred intention of the user. In some example embodiments, the MPAI system 40 creates an association between current sensor readings and the user's probable capabilities of completing a task of taking medicine.

IoT data 310 may include information received from various sensors available in the environment. Such sensors may be used for collecting status and/or usage data of monitored objects (e.g., meteorological data and water data, such as temperature, humidity; connected toothbrush usage; connected water bottle water consumption; connected coffee machine usage state; mattress pressure sensor sleep state reading; exercise regime participation as reported by a Cardio Vascular Rehabilitation system), interaction data (e.g., Virtual Personal Assistant (VPA) interactions; Medication dispenser interactions), and/or data from wearables (e.g., client devices devices such as phones, tablets, headsets, and the like to capture activity from accelerometers, screen state, particular app usage). Additionally or alternatively, the sensor data 312 provides any additional sensor information needed by the processor 212 which provides additional information in collecting activity and context data. The sensing modalities database 300 may include a prediction engine database which provides information needed by the processor 212 in training a prompting model/strategy and/or an adherence model/prediction using machine learning.

C. Exemplary Medical Prompting Artificial Intelligence (MPAI) System

MPAI system 40 can be configured to analyze existing medical adherence strategies derived from the existing population which most-nearly matches one or more characteristics of the user or from a default strategy. In certain embodiments, the MPAI system 40 may be embodied as a server and/or any other computing entity having one or more components as discussed above in reference to client devices 10A-10N. Moreover, the MPAI system 40 may be in communication (e.g., via communications network 20) with one or more client devices 10A-10N to provide an initial prompting model/strategy and/or adherence model/prediction for use via the prompting system, to provide various data usable via the medication prompting application, and/or the like. As discussed herein, the MPAI system 40 may be configured to continuously update one or more stored generic population prompting models, and accordingly the MPAI system 40 may be configured to receive data from the one or more client devices 10A-10N, and to store such data in a memory storage area similar to and/or embodied as a sensing modalities database 300 stored in association with the MPAI system 40.

For example, a default initial medicinal regimen prompting model/strategy learned for Alzheimer's patients may be more appropriate for Alzheimer patients than a prompting model/strategy appropriate for all members. The MPAI system 40 may be further configured to analyze the data in the sensing modalities database 300. In this way, the MPAI system 40 may support multiple algorithms and methodologies, including those discussed below with respect to determining a state of the environment and a state of the user based on the data from the sensing modalities database 300, analyzing the data together with existing and/or learned data to develop a medical adherence model/prediction to generate an effective prompting model/strategy.

Figure 4:
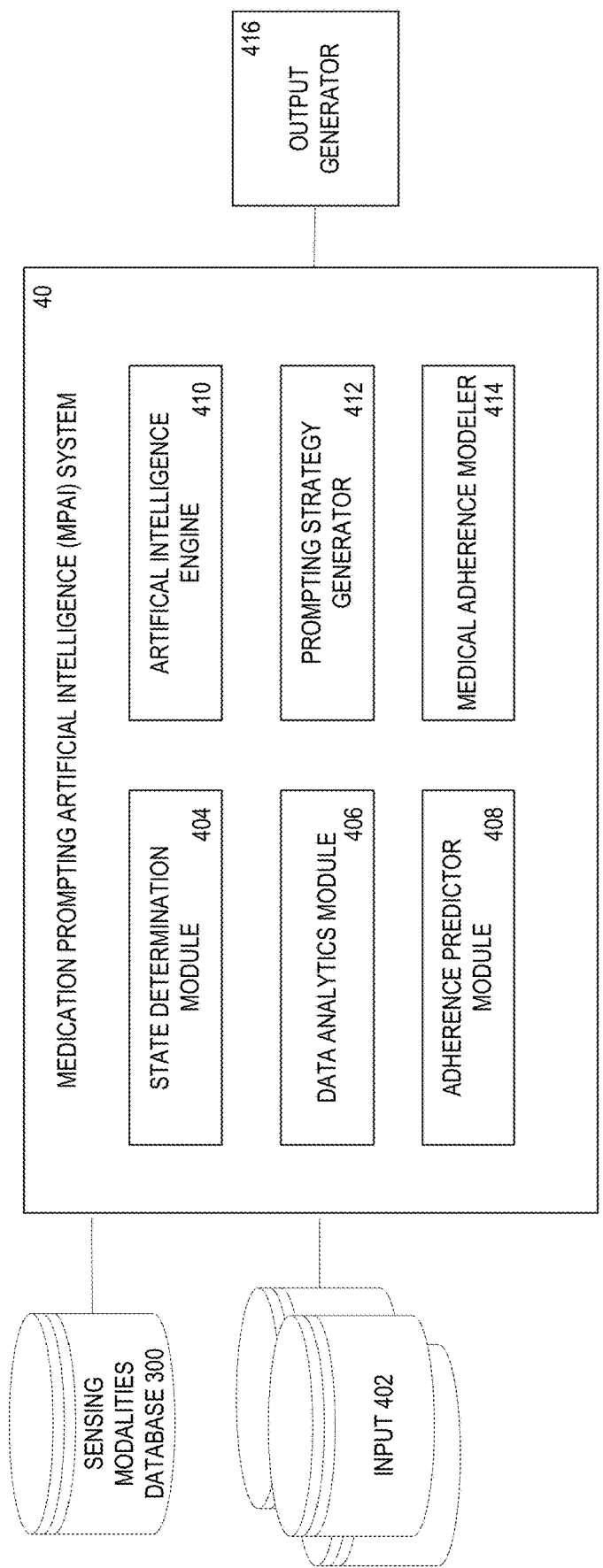
FIG. 4 illustrates an example MPAI system in accordance with some embodiments discussed herein.

In some embodiments, with reference to FIG. 4, the MPAI system 40 may include a state determination module 404, a data analytics module 406, an adherence predictor module 408, an artificial intelligence engine 410, a prompting model/strategy generator 412, and a medical adherence modeler 414, all of which may be in communication with the sensing modalities database 300. The MPAI system 40 may receive one or more environment and user context data and may generate the appropriate notifications to encourage medication adherence according to a medical adherence model/prediction using artificial intelligence. The MPAI system 40 may use any of the algorithms, operations, steps, and processes disclosed herein for receiving one or more environment and user context data, and generating the appropriate notifications to encourage medication adherence.

The MPAI system 40 may receive a plurality of inputs 402 from one or more client devices 10A-10N and process the inputs 402 within the MPAI system 40 to produce an output via an output generator 416, which may include appropriate prompting notifications, strategies, and/or messaging communications to improve task adherence (e.g., medication or treatment adherence). In some embodiments, the MPAI system 40 may execute user state and environment state determination using the state determination module 404, process the data in the data analytics module 406, predict conditions and timing for prompting events in the adherence predictor module 408, train prompting models/strategies and/or adherence models/predictions via the artificial intelligence engine 410, generate the predicted automated-prompting notifications in the prompting model/strategy generator, update the prompting models/strategies and/or the adherence models/predictions in the medical adherence modeler 414, and output the results via the output generator 416 which may, in turn, be configured to output one or more automated-prompting notifications via the communications circuitry 218 and/or any suitable client devices 10A-10N. Each of these steps may pull data from a plurality of sources including the sensing modalities database 300.

When inputs 402 are received by the MPAI system 40, an environment and/or a user state determination using the state determination module 404 may be made. An environment and/or a user state determination includes such information as a user or group medical policy data, when and whether the user completed the task of medical adherence, what type of prompt was provided and under what circumstances was the prompt initiated (e.g., audible prompt via a smart TV immediately after activity is observed and inputted). This information may give context to the user's environment and the user to determine the environment and user state. For example, the state determination module 404 may inform the MPAI system 40 as to the automated-prompting notifications to improve task adherence (e.g., medication or treatment adherence).

The MPAI system 40 may then compute the output using the data analytics module 406, the adherence predictor module 408, the artificial intelligence engine 410, the prompting model/strategy generator 412, and the medical adherence modeler 414. The data analytics module 406 draws information about the applicable profile data, environmental data, user capabilities data, IoT data, sensor data, prediction engine data from the sensing modalities database 300 and then, in light of the state determination module's 404 determination, analyzes the data to estimate the user's likelihood to adhere to a medication prompt over time based on the determined state of the user and the state of the environment. The data analytics module 406 is configured to predict the user's most likely activity levels over time and associate the user's activities or context with data from the environment states to better predict adherence. For example, knowing that the user will be active/not-active over the next period of time allows better estimation of his/her likelihood to adhere to a prompt over time. Forecasting of the user/state can be achieved in the artificial intelligence engine 410.

In some embodiments, the user's state, for example, may be indicative of activity level (e.g. from wearable sensors), stress level (e.g. from Galvanic Skin Response wearable sensor), conversation (e.g. from an ambient IoT Virtual Personal Assistant), and/or the like. The state of the environment may include presence of user within the environment (e.g. proximity of wearable IoT sensor to the home wireless network), the room which the user occupies (e.g. from Passive Infrared sensors), and/or the user's proximity to a medication dispenser (e.g. via detection of iBeacon, Eddystone or other Bluetooth Low Energy by the users personal IoT device).

The adherence predictor module 408 may be configured to estimate the user's likelihood to adhere to his/her medication given a particular sensed user/environment state. In some example embodiments, the adherence predictor module 408 estimates forecast adherence via one or more artificial intelligence and/or machine learning algorithms via the artificial intelligence engine 410. In certain embodiments, the artificial intelligence engine 410 may be generated at the MPAI system 40, and provided to one or more client devices 10A-10N for execution and/or updating. The artificial intelligence engine may provide a plurality of algorithms, which may utilize a generative approach, a discriminative approach, and/or other approaches for providing training data to the artificial intelligence algorithm. For example, in a generative approach, the training data may consist only of examples for successful medication prompts and the machine learning model learns to predict the likelihood of adherence in a given scenario. As an example of a generative approach, training data consists of both successful and unsuccessful prompt events and the model learns from both the positive and negative examples. Under the generative model, the artificial intelligence engine 410 may be configured to provide a likelihood value for a given feature. For example, the likelihood value may be indicative of a probabilistic measure or estimate that the user will take medication given the sensed user/environment. As various example methodologies in which the generative model can be provided, the artificial intelligence engine 410 may be configured to employ one or more of Naïve Bayes, Linear Discriminant Analysis, Regularized Discriminant Analysis, Quadratic Discriminant Analysis, Gaussian Mixture Models and Kernel Density Estimation.

Conversely, a discriminative approach, may comprise building a discriminative model to predict a users' likelihood to adhere or not adhere to a given medication prompt given the environment/user state at a particular time. Examples of how a discriminative model can be generated include Logistic Regression, Random Forests, Extreme Gradient Boosting and Deep Neural Networks.

With the artificial intelligence engine 410 configured to provide models for quantifying a user's predicted likelihood to adhere to medication prompting model/strategy over time, various artificial intelligence learning techniques may be utilized to train the prompting model/strategy and/or the adherence model/prediction to optimize future prompting strategies. As just one example, reinforcement learning can be applied to determine an optimal prompting model/strategy to maximize the likelihood of successfully prompting the user to take appropriate medication, which may be defined as the likelihood of successful medication adherence at optimal times. In reinforcement learning, a policy for performing some action, π is defined as:

$$\pi(a|s)=P(a_t=a|s_t=s),$$

A particular policy π generated and/or determined based on the foregoing is reflective of the probability that the MPAI system will take a particular action $a_t$ (e.g., prompt to take prescribed medicine) when the environment (e.g., user activity, user location, whether the user has already performed the action, and/or the like) is in a particular state $s_t$. The action $a_t$ may be utilized to determine whether and/or when to prompt the user and/or which prompting modality (e.g. which device and type of prompt—beep, on-screen notification, auditory, and/or the like) should be utilized to maximize the probability that the user will take the particular action. Throughout the present disclosure, it should be understood that the term "modality" includes the classification of a particular device and/or a channel of sensory input/output between a device (e.g., a computing device) and a user.

The prompting model/strategy generator 412 may be configured for such reinforcement learning (and/or other types of learning) in which a prompting model/strategy for sending the user medication prompts is generated, such that the long-term expected value to the user is maximized. The prompting model/strategy generator 412 is configured to calculate an expected value for a chosen policy over time based on the starting state and the policy as:

$$V_\pi(s)=E[\Sigma_{t=0}^\infty \gamma^t r_t|s_0=s]$$

where $r_t$ is the reward (e.g., reflective of a likelihood of success) at step t and γ is the discount rate that specifies the tradeoff between immediate reward and longer-term reward. With these equations defined for this problem, the prompting model/strategy generator 412 can use standard reinforcement learning techniques to generate a prompting model/strategy for the user which maximizes the long-term adherence for the user.

As indicated, while a particular embodiment of this invention uses reinforcement learning to decide upon the optimal medication prompting schedule, alternative embodiments include using Model Predictive Control, Genetic Algorithms, Particle Swarm Optimization, Simulated Annealing, grid search, and/or a variety of other techniques and methodologies to determine the optimal medication prompting model/strategy given the aforementioned medication adherence models.

Based on the generated prompting model/strategy for the user which maximizes the long-term. adherence for the user information as well as the applicable one or more interaction modalities, the MPAI system 40 may be configured to determine an appropriate output via the output generator 416, such as presenting the one or more interaction modalities in the IoT device and/or presenting associated automated-prompting notifications via the communications circuitry of one or more client devices 10A-10N.

The MPAI system 40 may also determine an optimal, primary prompting model/strategy to be generated such as the time to prompt the user to take his/her medication. The MPAI system 40 may also determine secondary prompting strategies such as whether to prompt the user at all in which some users might benefit more from receiving prompts infrequently and only when they are highly likely to fail to adhere to their medication regime. In such instances, the MPAI system 40 may be configured to determine the appropriate device (e.g., mobile phone, TV, Google Home, Alexa) and prompting modalities (e.g., voice, text, message, overlay notification) to use in instances in which the environment has multiple devices. Even in instances in which only one device exists, that device may have multiple interaction modalities and accordingly the MPAI system 40 may be configured to choose the optimal prompting device and modality based at least in part on a user's given user state and/or environment state. The result of the unique combination of techniques from artificial intelligence and IoT leads to maximizing the user's medication adherence over time which can significantly increase quality of life for users.

As will be appreciated, one or more of the MPAI system 40 components may be located remotely from other components, such as in a distributed system. Furthermore, one or more of the components may be combined and additional components performing functions described herein may be included in the MPAI system 40. Thus, the MPAI system 40 can be adapted to accommodate a variety of needs and circumstances.

IV. EXEMPLARY SYSTEM OPERATION

The operation of various embodiments of the present invention will now be described. As discussed herein, various embodiments are directed to systems and methods for providing users with reminder prompts to take a particular action, such as taking a prescribed medication. These prompts may be provided via one or more computing entities that are dynamically identified via the prompting apparatus.

A. User Registration

As noted, each user may have a profile accessible via the MPAI system 40 and/or stored via one or more client devices 10A-10N. For example, a user can input various information to register/enroll and create or update a user profile for storage and use by the MPAI system 40 and/or stored via one or more client devices 10A-10N. Such profiles can be created, stored, edited, and/or customized manually, automatically, and/or semi-automatically to adapt to various needs and circumstances.

To provide appropriate prompts for a user, the MPAI system 40 (via the one or more client devices 10A-10N) is configured to receive and store user profile data 304 for one or more individual users. As discussed herein, the user profile data 304 comprises data indicative of a medicinal treatment regimen applicable for the user, as well as data indicative of one or more devices that may be utilized to provide prompts and/or one or more devices that may be utilized as sensor input data generation sources for the user to provide ongoing training data for a user's particular prompting model/strategy and/or adherence model/prediction.

Moreover, the user profile data 304 may comprise user identifier data, such as a user name, a password, a user's real name, contact information (e.g., phone number, email address, mailing address, and/or the like). Such identifier data may be utilized to synchronize and/or link various devices (e.g., sensor devices, prompting devices, and/or the like) for operation with the user's prompting system, as discussed herein.

In certain embodiments, the profile data 304 may comprise care provider data indicative of one or more care providers associated with the user. For example, a physician, a family member, a friend, and/or other individuals associated with the user may be reflected within the profile data 304 for the user. The care provider data may comprise care provider identity data (e.g., a care provider's name and/or title) as well as contact information for the care provider (e.g., phone number, email address, and/or the like). In certain embodiments, care providers may have associated user profile data 304 stored in association with the MPAI system 40, and in such embodiments the MPAI system 40 may be configured to provide data indicative of a user's adherence to an applicable medicinal treatment regimen via prompts provided to client devices associated with the care provider.

To register a user, an individual (e.g., the user, a care provider associated with the user, and/or the like) may provide identifying information about the user to the MPAI system 40 and/or the one or more client devices 10A-10N for storage, for example, in the sensing modalities database 300. The identifying information may be provided via an interactive user interface displayed via a client device 10. The interactive user interface may be configured to accept user input indicative of the profile data 304 for the particular user. Moreover, the interactive user interface may be configured to accept user input indicative of treatment data providing a prescribed medicinal treatment regimen for the user. The treatment data may specify a treatment type (e.g., prescription medicine), an activity type (e.g., consume one pill of a specified medicine type), a prescribed timing (e.g., one pill each morning and one pill each evening), and/or the like. The interactive user interface may additionally be configured to accept additional characterizing data about the user, for example, the type of medical condition associated with the user, the user's age, the user's gender, the user's physical condition, and/or the like.

In one embodiment, the treatment data may be provided based as least in part on an assessment regarding the user's individual medical needs. The assessment may be guided by user interfaces generated at least in part by the MPAI system 40, which may be configured to accept user input from a user indicative of his/her ideal medicinal regimen. Additionally or alternatively, the ideal medicinal regimen as well as medication directions may be automatically entered by a prescription management system in communication with the MPAI system 40. In yet other embodiments, the ideal medicinal regimen may be determined automatically by the MPAI system 40, for example, based on machine-learning models of medicinal regimens for other users having similar medical conditions, based on automatically retrieved data from an external information source (e.g., a care provider's medical records system), and/or the like.

Upon receipt of the user input, the MPAI system 40 may generate a user profile comprising the profile data 304 within the sensing modalities database 300 for storing data associated with the user. Moreover, upon generation of the user profile, the MPAI system 40 may assign an initial prompting model/strategy and/or adherence model/prediction to the user to be stored in association with the user profile. As discussed herein, the MPAI system 40 may store a plurality of initial prompting models/strategies and/or adherence models/predictions each applicable for different user characteristics (e.g., various prompting models/strategies and/or adherence models/predictions each corresponding to a particular medical condition, a particular age, a particular gender, and/or the like). Thus, the MPAI system 40 may be configured to select an initial prompting model/strategy and/or adherence model/prediction to be assigned to the user profile that is most-applicable to the user characteristics identified within the user profile. As a specific example, upon generation of a user profile for a diabetic, 50 year old male patient, the MPAI system 40 may be configured to select an initial prompting model/strategy and/or adherence model/prediction generated for treatment of a diabetic male patient between the ages of 40-55.

As discussed herein, the initial prompting model/strategy and/or adherence model/prediction may be generated to provide prompts to a user via one or more client devices 10A-10N based on collective learnings of prompts provided to other patients having similar characteristics. In certain embodiments, the initial prompting models/strategies and/or adherence models/predictions stored via the MPAI system 40 may be continuously evolving (e.g., through machine learning based at least in part on data generated by each of a plurality of individual users).

With reference again to the registration process, the MPAI system 40 may be configured to receive data indicative of one or more devices associated with the user. In certain embodiments, the MPAI system 40 may automatically generate and/or store data indicative of the various devices associated with the user, in response to log-in requests for the user received from various devices. For example, users may download and install software applications on one or more electronic devices (e.g., computers, mobile devices, wearable computing devices, and/or the like), and may provide identifying information (e.g., log-in credentials) via a user interface provided through the installed software program on each of the client devices. Upon logging into the software program on each of the client devices, the MPAI system 40 may be configured to collect device data regarding each device providing the user identifying data and may store the device data in association with the user profile. In certain embodiments, the device data may comprise device identifying data (e.g., IP address, MAC address, device name, and/or the like), and/or device capabilities data. The device capabilities data may be indicative of whether the device is usable for providing automated-prompting notifications (e.g., reminder prompts) received from a client device 10, for generating sensor data (e.g., indicative of user and/or environmental data), and/or the like.

In certain embodiments, device data may further be provided manually and/or via interactions with other computing systems. For example, a user may provide device identifying data (e.g., an IP address) for a plurality of IoT devices (e.g., thermostats, proximity sensors, flowmeters, and/or the like) to be associated with the user profile and for providing sensor data for the user profile. As yet another example, the MPAI system 40 may be in communication with other, external systems, such as a thermostat monitoring system (e.g., central servers associated with one or more IoT enabled thermostats), and accordingly the MPAI system 40 may be configured to automatically request and/or retrieve device identifying data for each of one or more devices from the external system.

Once a user is registered, the MPAI system 40, via one or more client devices 10A-10N, may be configured to generate prompts via one or more registered devices for the user and/or to receive sensor data from the one or more devices, as indicated by the device capabilities data.

B. Activity Monitoring and Prompting

Figure 5:
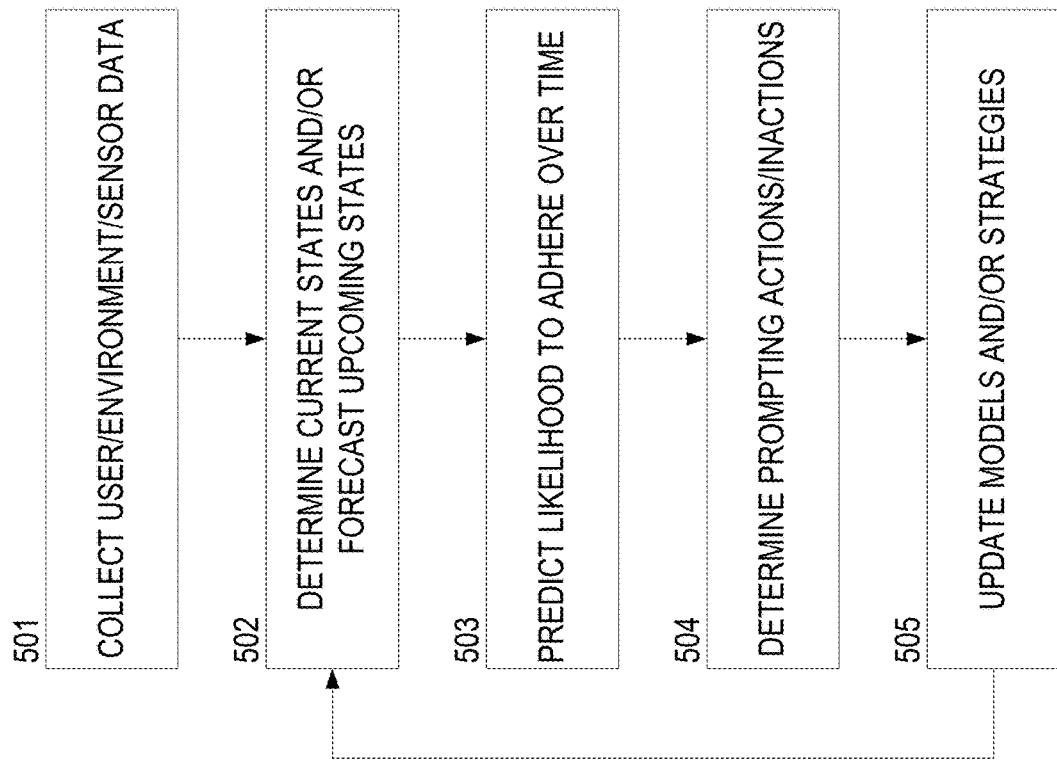
FIG. 5 illustrates a flow diagram of an example MPAI system in accordance with some embodiments discussed herein.

FIG. 5 specifically illustrates an example flowchart providing various operations, steps and processes for monitoring user and/or environmental characteristics (e.g., environmental context data) for a particular user, via the MPAI system 40 and/or the one or more client devices 10A-10N or other user-specific devices. Via the various steps of FIG. 5, a user's adherence to the medicinal regimen or schedule may be performed in real-time or near real-time with the MPAI system 40 and/or the client devices 10A-10N interacting with the user (e.g., via one or more devices providing prompts to the user and/or generating sensor data regarding the user). Such interactions (whether in real-time or not) may include feedback, status changes, encouragement, and/or a variety of other verbal and non-verbal interactions. Examples include: encouraging a user to make more positive exercise choices by reminding the user to exercise at times learned to maximize his/her likelihood to exercise; encouraging user to make more mental-health-positive choices by calling a family member at an optimal time; reminding a medical professional to write-up his/her observations at times most likely to be available for documentation; and/or reminding a patient to eat healthy snacks at times they are most likely to be hungry between meals.

Immediately after registration of the user, user prompts for various activities may be provided according to a general prompting model/strategy and/or adherence model/prediction generated based at least in part on data generated for a population of users having characteristics similar to the particular user. Thus, prompts for scheduled activities (e.g., taking a medication) may be provided at, or temporally proximate to the exact scheduled time for the various activities, regardless of the user's current activities (or based at least in part on determined characteristics of the population reflected in the general prompting model).

However, as indicated at Block 501 of FIG. 5, the MPAI system 40 and/or various client devices 10A-10N begin collecting data from the various sensor 15A-15N (e.g., those devices having associated device capabilities data indicating the device is usable as a sensor device) monitoring user characteristics (e.g., user context data) and/or environmental characteristics (e.g., environmental context data). In certain embodiments, the sensor data may be provided and/or stored at a highly-generic level to preserve a high degree of patient privacy. For example, data generated and provided from an accelerometer in a wearable computing device may be stored simply as data generated by a generic "Sensor 1" without an indication as to the type of sensor utilized. In such embodiments, the MPAI system 40 (and/or one or more client devices 10A-10N executing a prompting model/strategy and/or adherence model/prediction thereon) may be configured to predict whether a particular sensor (e.g., a generic "Sensor 1") is likely to be at a particular state (e.g., generating a particular type of output) for a future period of time, and to determine whether this particular state is likely to impact the user's predicted likelihood of adhering to provided automated-prompting notifications (e.g., reminder prompts).

In other embodiments, data regarding the type of sensor utilized may be collected and stored to provide additional data that may be utilized to develop trends and/or characteristics of the likelihood that the user will perform a particular action. For example, data collected from the accelerometer mentioned previously may be utilized to develop trends. For example, based on a specific detected combination of movements by the accelerometer (e.g., detected at the beginning of a user's workout routine, for example), the MPAI system 40 and/or the one or more client devices 10A-10N may be configured to predict that the user will likely remain active for at least a predetermined period of time). The MPAI system 40 and/or the one or more client devices 10A-10N need not determine the exact activity being performed by the user, but the MPAI system 40 and/or the one or more client devices 10A-10N may still collect data indicating that the user is likely to remain busy for a predetermined period of time based on learned trends from historical data collections. As a specific example, if a user always begins a 1-hour workout with a 5-minute warm-up on an elliptical machine, followed by a 10-minute stretching routine, the MPAI system 40 and/or the one or more client devices 10A-10N may be configured to determine that the user will likely remain busy for approximately 60 minutes after detecting the combination of movements associated with the user's warm-up routine (even if the MPAI system 40 and/or the one or more client devices 10A-10N do not specifically recognize that the user is performing an exercise routine).

As yet another example, the MPAI system 40 and/or the one or more client devices 10A-10N may collect data indicative of an average length of time that a user typically spends watching television at various times of day. Thereafter, the MPAI system 40 and/or the one or more client devices 10A-10N may be configured to estimate the average amount of time that the user is likely to remain stationary while watching TV depending at least in part on the time at which the user first turns on the TV (as detected based on signals transmitted from the TV to the MPAI system 40 upon initialization).

The MPAI system 40 and/or the one or more client devices 10A-10N may be configured to detect any of a variety of user (e.g., user context data) and/or environmental characteristics (e.g., environment context data) to be associated with a user. As discussed in greater detail in reference to Block 505, below, the prompting model/strategy and/or adherence model/prediction is updated over time to reflect the detected correlation between various detected current activities and likely future activities. Over time, the prompting model/strategy and/or adherence model/prediction may be updated to determine whether a particular sensor output is indicative of future behavior or not, and accordingly the MPAI system 40 and/or the one or more client devices 10A-10N may determine over time that certain sensory outputs may be ignored or given greater predictive weight. For example, the MPAI system 40 and/or the one or more client devices 10A-10N may determine that various sensors are indicative of activities of other, non-user individuals (e.g., housemates of the user), and accordingly reliance on these sensors should be minimized (e.g., entirely, during particular times of day, and/or the like) to avoid diluting the effectiveness of the sensor system. For example, if movement is detected in a kitchen area, but the user is operating his or her phone in the bedroom, the MPAI system 40 and/or the one or more client devices 10A-10N may determine that the motion in the kitchen is not associated with the user.

Thus, the various sensors may be configured to detect user characteristics (e.g., user context data), such as sleep state (awake or asleep); activities such as eating, drinking, exercising, sitting, standing, typing, and/or the like; user location; a user's gestational status, and/or the like. Various sensors may also detect a plurality of environmental characteristics (e.g., environmental context data), such as proximity of the user to a medicinal container, electronic device status (e.g., TV initiated, TV channel on, activity of a mobile device, and/or the like), pressure sensor status (e.g., whether a user is laying on a bed or sitting in a chair), who a user is calling via a telephone, flow meter status (e.g., whether a kitchen faucet is on/off, whether a shower faucet is on/off, whether a gas stove is on/off, and/or the like), whether various lights are on/off (e.g., lights in exercise room, lights in office, and/or the like), and/or the like. In certain embodiments, the environmental sensors may detect characteristics of the user as well. For example, a sound-based sensor (e.g., a phone microphone, a voice-activated personal assistant, and/or the like) may monitor the user's speech tone and/or other characteristics (e.g., high pitch, low pitch, volume, talking speed, word choice, and/or the like).

In yet other embodiments, the sensor data may comprise data indicative of a user's schedule. Thus, at least a portion of the sensor data may be embodied as calendar data retrieved from one or more client devices 10A-10N associated with the user. Based on the calendar data, the MPAI system 40 and/or the one or more client devices 10A-10N may be configured to determine if a user is scheduled to be busy during an optimal time for taking a prescription medication, and therefore the and/or the one or more client devices 10A-10N may be configured to provide a prompt to the user prior to the start of a scheduled event.

The MPAI system 40 and/or the one or more client devices 10A-10N may be configured to train the prompting model/strategy and/or adherence model/prediction based at least in part on the user-specific data generated for the user by the one or more sensors 15A-15N. As indicated at Block 502 of FIG. 5, with the user context data and the environment data, the MPAI system 40 and/or the one or more client devices 10A-10N may determine a current user state and or a current environmental state. Further, the MPAI system 40 and/or the one or more client devices 10A-10N may be configured to forecast upcoming states (e.g., a future user state and a future environmental state) associated with the user based at least in part on the determined current state of the user, the determined current state of the environment, and/or the user-specific trained prompting model/strategy and/or adherence model/prediction.

Moreover, the MPAI system 40 and/or the one or more client devices 10A-10N may be configured to receive data indicative of adherence to a prescribed medicinal therapy regimen from one or more sensors 15A-15N. For example, an IoT connected medicine container may be configured to monitor user access to or the weight of the medicine container, which the MPAI system 40 and/or the one or more client devices 10A-10N may associate with taking medicine from the container. As yet other example, the MPAI system 40 and/or the one or more client devices 10A-10N may be configured to accept user input data indicative of whether the user took medicine (e.g., based on user input provided via an interactive graphical user interface provided via a client device 10). As yet another example, the MPAI system 40 and/or the one or more client devices 10A-10N may receive data from one or more sensing devices (e.g., an accelerometer within a wearable computing device) indicative of user activities associated with taking a medicinal treatment. As a specific example, an accelerometer may record data indicative of user movements to unscrew a medicine container cap, and to move the user's hand/wrist toward the user's mouth while placing a pill in the user's mouth.

Figure 6:
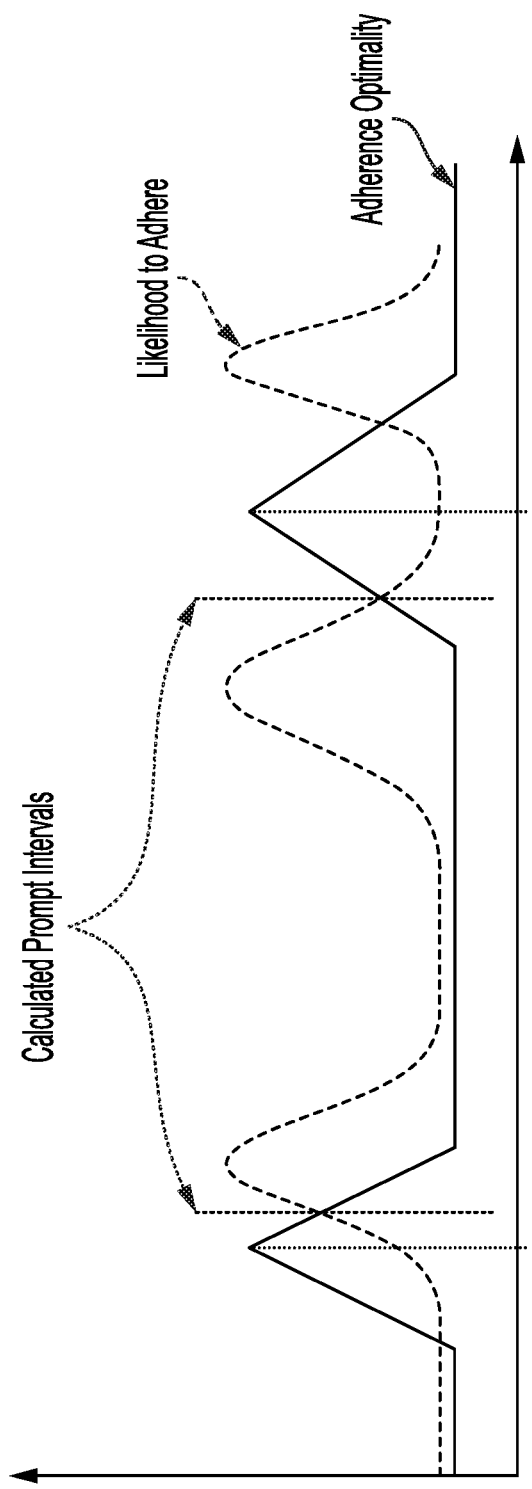
FIGS. 6, 7, 8A, 8B, and 8C are outputs produced by various embodiments of the present invention.
Figure 7:
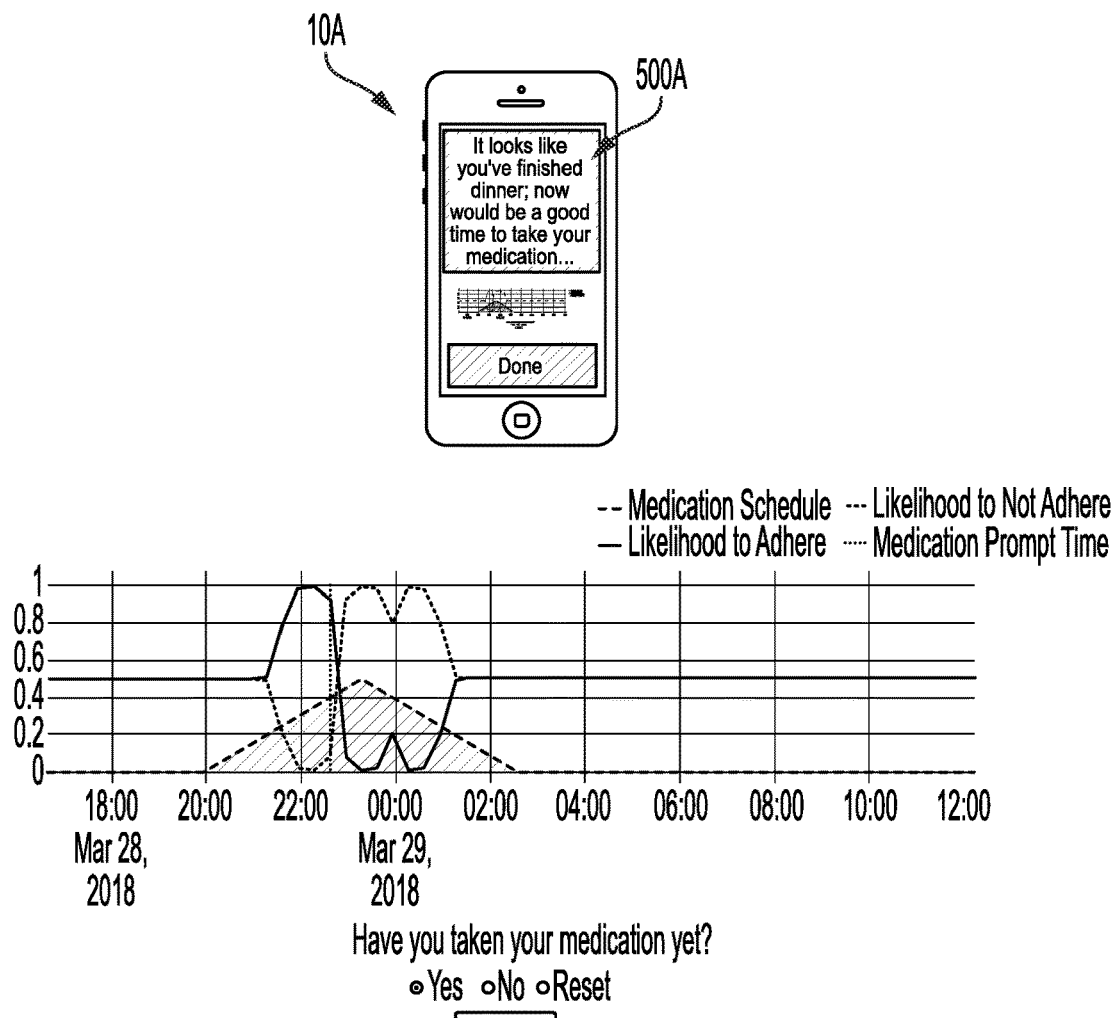

As a part of the training process discussed herein, the MPAI system 40 may be configured to identify correlations between determined current user states and/or environmental states associated with the user and a likelihood that the user will adhere to a particular medicinal therapy regimen. FIGS. 6-8 illustrate graphical representations of the likelihood of a user complying with applicable medicinal therapy regimens. With reference first to FIG. 6, a first example is illustrated graphically as a function of time (along the horizontal axis). The line indicated as illustrating "adherence optimality" illustrates optimal times to take an example medication at the top of the triangular peaks (and as reflected by the dashed lines). The optimality of timing decreases on either side of the peak time, however there remains some therapeutic benefit to taking the medicine during any time that the adherence optimality line is above the minimum level. Also shown in FIG. 6 is a line indicative of the likelihood of the user adhering to automated-prompting notifications (e.g., reminder prompts) to take a prescribed medicine. As indicated in the example of FIG. 6, there are three periods of time when the user's likelihood of adherence increases above a minimum, as indicated by the wave-shaped peaks within the "likelihood to adhere" curve. This curve is reflective of the result of the MPAI system 40 and/or one or more client devices' 10A-10N determination of a user's likelihood to adhere to prompts, as indicated at Block 503 of FIG. 5.

Based at least in part on the determined likelihood that user will adhere with automated-prompting notifications (e.g., reminder prompts), the prescribed timing for performing the therapeutic action (e.g., taking prescription medication), and the forecast of upcoming user states, the MPAI system 40 and/or the one or more client devices 10A-10N are configured to determine what modalities and types of prompting actions are most appropriate for the user and when those prompting actions should occur, as indicated at Block 504 of FIG. 5. With reference to the illustrated embodiment of FIG. 6, the MPAI system 40 and/or the one or more client devices 10A-10N determine the optimal prompting time to be the highest intersection of the adherence optimality curve and the likelihood to adhere curve within the graphical illustration (indicated with the vertical lines extending through the intersections of the curves). This point is indicative of a determined time in which complying with the prescribed medicinal treatment remains effective, and the user is most likely to comply with automated-prompting notifications (e.g., reminder prompts). It should be noted that this point may not be the point at which the MPAI system 40 and/or the one or more client devices 10A-10N determine that the user is most-likely to comply with a reminder prompt. Instead, the determined time for providing a prompt is determined as an optimal balance between likelihood of user compliance and predicted effectiveness of adhering with the prescribed medicinal therapy regimen. Moreover, as indicated on the right side of FIG. 6, in instances in which the MPAI system 40 and/or the one or more client devices 10A-10N predict a plurality of optimal prompting times surrounding a particular medicinal treatment regimen schedule, the MPAI system 40 and/or the one or more client devices 10A-10N may default to providing a prompt prior to the optimal time for complying with the medicinal therapy regimen, such that the one or more client devices 10A-10N may provide a second prompt at the second predicted time in the event the user does not comply with the first prompt.

In certain embodiments, the MPAI system 40 and/or the one or more client devices 10A-10N may be configured to detect an appropriate time for generating a reminder prompt for a user based at least in part on a detected occurrence of a trigger event. For example, upon the detected completion of a high-activity period (e.g., after an exercise routine is completed), upon the detected presence of a user within the same room as prescribed medicine, and/or the like, the one or more client devices 10A-10N may be configured to generate a reminder prompt to be provided to the user.

In addition to determining an appropriate time to generate a prompt for the user, the MPAI system 40 and/or the one or more client devices 10A-10N are further configured to determine an appropriate modality for providing a prompt to the user. As discussed here, the user profile comprises device capability data indicating whether each registered device is configured for providing prompts to the user, and the modalities available for each device. Thus, the MPAI system 40 and/or the one or more client devices 10A-10N are configured for determining an appropriate device for providing prompts to the user to maximize the likelihood of adherence with the medicinal therapy regimen, as well as the appropriate modality within the selected device (e.g., tactile notification, visual notification, audible notification, and/or the like) for generating the prompt. In certain embodiments, the MPAI system 40 and/or the one or more client devices 10A-10N may predict which device a user is most likely to pay attention to (e.g., a TV if the TV is active, a mobile phone if the user is located away from home, a voice-based virtual digital assistant if the user is in the same room as the digital assistant, and/or the like), based at least in part on the user characteristics (e.g., user context data), environmental characteristics (e.g., environmental context data), prompting model/strategy, and/or adherence model/prediction. The selected one or more client devices 10A-10N thus generate a prompt for the user.

FIG. 7 illustrates just one example prompt 500A that may be provided to a user, as well as the time at which the prompt is provided. Looking first at the graphical depiction showing the user's likelihood of compliance over time (which may be determined based at least in part on a user-trained prompting model) relative to the optimal time of compliance (indicated at the peak of the shaded triangle), the MPAI system 40 and/or the one or more client devices 10A-10N determines the optimal time for providing a prompt to be at approximately 2300 hours, as reflected by the vertical line shown in the graph. Now referencing the example interactive user interface, the MPAI system 40 determines the most-appropriate prompting modality is to provide a pop-up notification, in this example, via a mobile device carried by the user. In certain embodiments, the notification may provide a graphical indication of why the prompt is provided at the specified time (e.g., the prompt may include the graphical depiction shown at the bottom of FIG. 7). As other examples, the one or more client devices 10A-10N may be configured to generate audible (e.g., voice-based, tone-based, and/or the like) reminders for the user, tactile reminders for the user (e.g., generated by a wearable computing device), visual based reminders (e.g., a flashing light, a displayed message, and/or the like), and/or the like.

As discussed herein, the MPAI system 40 and/or the one or more client devices 10A-10N are configured to detect whether the user complied with the medicinal therapy regimen, and the MPAI system 40 is configured to determine correlations between the prompting time and/or prompting modality utilized and the likelihood of compliance for the user. This data may be utilized to train the prompting model/strategy and/or adherence model/prediction using at least the techniques discussed above, as indicated at Block 505 of FIG. 5.

Figure 8A:
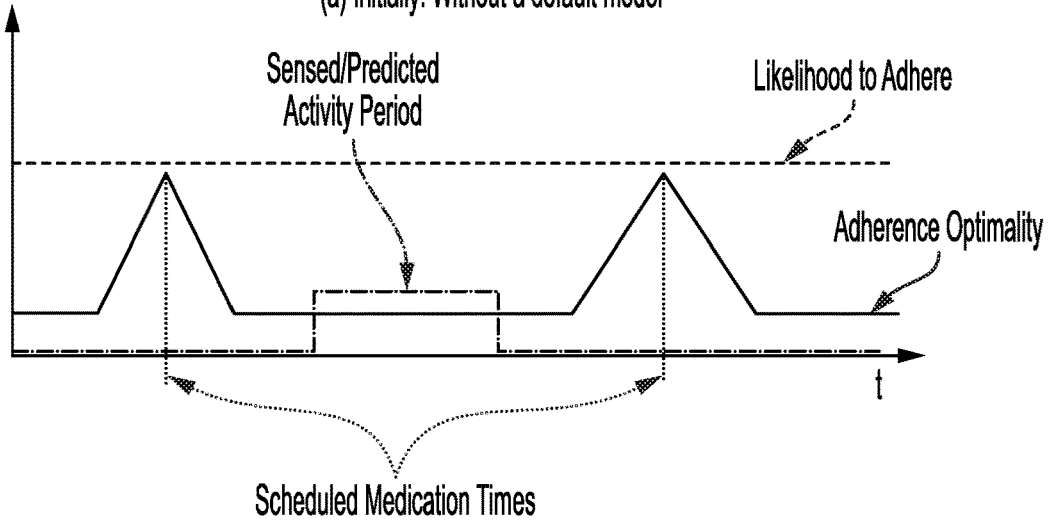
Figure 8B:
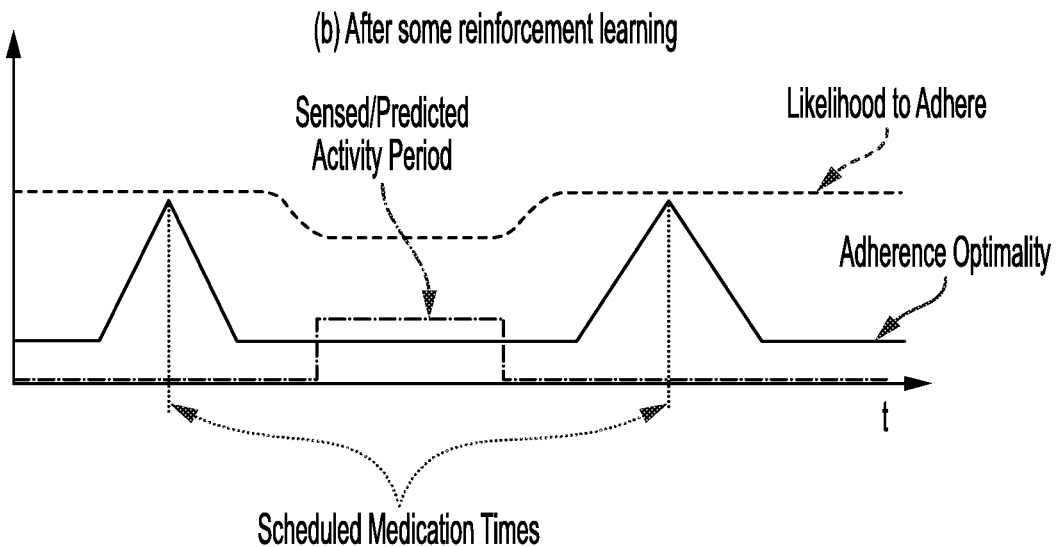
Figure 8C:
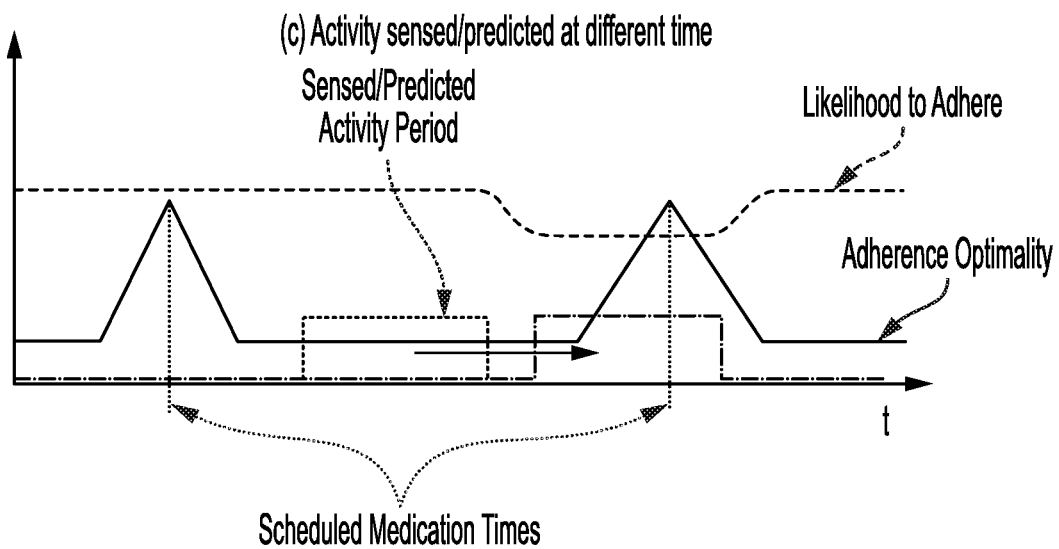

The various graphical representations shown in FIGS. 8A-8C provide an example result of training the prompting model/strategy and/or adherence model/prediction for a particular user. As indicated at FIG. 8A, the prompting model/strategy and/or adherence model/prediction may not have any knowledge regarding correlation between user activity and the likelihood of adhering with the prompt, and accordingly the "likelihood to adhere" curve is illustrated as a horizontal line (in this example, the prompting model/strategy and/or adherence model/prediction does not encompass any knowledge that may be gleaned from an example population, however it should be understood that similar methodologies may be provided for training a prompting model/strategy and/or an adherence model/prediction that is initially generated based on data for a general population).

Over time, the MPAI system 40 and/or the one or more client devices 10A-10N executing the prompting model/strategy and/or adherence model/prediction correlate the illustrated "sensed/predicted activity period" with a decreased likelihood of adherence with provided prompts, and therefore the "likelihood to adhere" curve is adjusted to decrease during periods of time that the user is detected to be active, as indicated in FIG. 8B. However, in the illustrated instances of both FIGS. 8A-8B, the detected activity period does not overlap with the scheduled medication times, and therefore the appropriate prompting time remains coextensive with the scheduled medication times.

Using this training, the MPAI system 40 and/or the one or more client devices 10A-10N are configured to detect an appropriate prompting time when the detected activity period overlaps with a scheduled medication time, as indicated at FIG. 8C. As shown therein, as the detected activity period is moved to overlap with the second scheduled medication time, the likelihood of adhering with provided prompts decreases at a time corresponding to the detected activity period. Thus, in the instance of FIG. 8C, the MPAI system 40 and/or the one or more client devices 10A-10N may determine that the appropriate prompting time is after the predicted activity period ends, but before the predicted effectiveness of the medication is rendered moot. The illustrated embodiment of FIGS. 8A-8C shows an example reinforcement-learning techniques in the machine learning context for training the prompting model/strategy and/or adherence model/prediction, by which prompting model/strategy and/or adherence model/prediction determines an appropriate prompting model/strategy and records whether the determined prompting model/strategy was effective. However, it should be understood that any of a variety of artificial intelligence learning mechanisms may be utilized, including Model Predictive Control, Genetic Algorithms, Particle Swarm Optimization, Simulated Annealing, grid search, and/or a variety of other techniques and methodologies to supervised or unsupervised learning, to reach a desired level of prompting effectiveness.

Moreover, the MPAI system 40 and/or the one or more client devices 10A-10N may detect over time that adherence with a particular medicinal therapy regimen increases for a user, and as a consequence, the MPAI system 40 and/or the one or more client devices 10A-10N may determine that the user relies less heavily on automated-prompting notifications (e.g., reminder prompts). The MPAI system 40 and/or the one or more client devices 10A-10N may continue to modify the prompting model/strategy and/or adherence model/prediction for the particular user based on such determinations, and may decrease the number and/or forcefulness of automated-prompting notifications (e.g., reminder prompts) provided to the user. Ultimately, the MPAI system 40 and/or the one or more client devices 10A-10N may be configured to generate automated-prompting notifications (e.g., reminder prompts) only in instances in which the user's likelihood of compliance with the medicinal therapy regimen without prompts is particularly low, and in such instances the MPAI system 40 and/or the one or more client devices 10A-10N may determine a most-appropriate time for generating prompts to maximize the likelihood that the user will comply with those prompts, in a manner as discussed herein.

C. Consequential Actions

In certain embodiments, the MPAI system 40 may be configured to perform one or more consequential actions upon detecting a lack of compliance with a prescribed medicinal therapy regimen after providing various prompts to a user. For example, the MPAI system 40 may be configured to generate one or more alerts to be provided to a care provider (e.g., via prompts provided via the system of the MPAI system 40, or via contact information provided within the user profile), such that the care provider may take appropriate remedial action if necessary.

Moreover, the user's adherence may be tracked via a care provider-accessible tracking user interface that enables the care provider to have visibility into the user's adherence with a prescribed medicinal therapy regimen. Thus, upon detecting a particularly low rate of adherence, the care provider may appropriately adjust the medicinal therapy regimen for the user to accommodate the low adherence rates and/or to compensate for the prior low adherence rates.

D. General Model Updates

As discussed herein, in the MPAI system 40 may be further configured to constantly update general population models (e.g., those models applied for new users) based at least in part on data retrieved for individual users. Thus, in addition to using adherence data to update the user's individual prompting model/strategy and/or adherence model/prediction, the adherence data for a plurality of users may be compiled and utilized to train a general-population model for new users. In certain embodiments, the general population models may be provided for populations having shared user characteristics (e.g., a diabetic patient model; an HIV-positive patient model; an 18-24 year old male model; and/or the like), such that the general models may be tailored to various user characteristics (e.g., user context data) that may be determined to correlate to the effectiveness of various prompting models. Thus, data for specific individuals having shared user characteristics (e.g., user context data) may be compiled and utilized to train a general-population models for new users of the prompting apparatus system.

V. CONCLUSION

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

For example, the foregoing description provides various examples of utilizing systems and methods for providing automated-prompting notifications (e.g., reminder prompts) for users to take medication. However, it should be understood that various embodiments of the systems and methods discussed herein may be utilized for providing reminders of any activity, such as exercising, eating healthy snacks, performing a particular task, calling another individual, and/or the like.

The invention claimed is:

1. An apparatus comprising at least one processor and at least one memory including computer program code for one or more programs, the at least one memory and the computer program code configured to, with the at least one processor, cause the apparatus to perform at least the following:
store a schedule comprising a task to be performed by a user;
provide a first automated-prompting notification to the user to perform the task;
determine that the user completed the task responsive to the first automated-prompting notification, wherein (a) a first state of the user and a first state of the user's environment are stored in association with the first automated-prompting notification, (b) the first state of the user, the first state of the user's environment, and the first automated-prompting notification are used to train a prompting model using machine learning, and (c) the prompting model outputs one or more automated-prompting notifications;
detect a first input indicative of a context of an environment of the user;
detect a first input indicative of a context of the user;
determine, based at least in part on the first input indicative of the context of the environment of the user and the first input indicative of the context of the user, a second state of the user and a second state of the user's environment;
determine, based at least in part on the second state of the user, the second state of the user's environment, and the prompting model, a second automated-prompting notification; and
provide the second automated-prompting notification.

2. The apparatus of claim 1, wherein the at least one memory and the computer program code are further configured to, with the at least one processor, cause the apparatus to perform at least the following:
determine that the user completed the task responsive to the second automated-prompting notification; and
train the prompting model using machine learning based at least in part on the second state of the user, the second state of the user's environment, and the second automated-prompting notification.

3. The apparatus of claim 2, wherein the at least one memory and the computer program code are further configured to, with the at least one processor, cause the apparatus to perform at least the following:
detect a second input indicative of a context of an environment of the user;
detect a second input indicative of a context of the user; and
determine, based at least in part on the second input indicative of the context of the environment of the user and the second input indicative of the context of the user, a future state of the user and a future state of the user's environment; and
determine, based at least in part on the future state of the user and the future state of the user's environment, a prompting model.

4. The apparatus of claim 1, wherein the first input indicative of the context of the environment of the user is selected from the group consisting of an activation state of a device, a proximity to an object, a proximity to a device, and a sound.

5. The apparatus of claim 1, wherein the first input indicative of the context of the user is selected from the group consisting of a movement of the user, an activity of the user, an action of the user, a gesticulation of the user, a vocal expression of the user, a facial expression of the user, a schedule of the user, a visual perception of the user, an auditory perception of the user, a tactile perception of the user, a cognitive load of the user, a social restriction of the user, an interaction of the user with a device, and interaction of the user with other users, an interaction of the user with a medical dispenser, an interaction of the user with services, and an inferred intention of the user.

6. The apparatus of claim 1, wherein the at least one memory and the computer program code are further configured to, with the at least one processor, cause the apparatus to perform at least the following:
control an output of a particular device by providing at least one control signal to the particular device.

7. The apparatus of claim 6, wherein the prompting model is trained using the generative approach comprising at least one of Naïve Bayes, Linear Discriminant Analysis, Regularized Discriminant Analysis, Quadratic Discriminant Analysis, Gaussian Mixture Models, or Kernel Density Estimation.

8. The apparatus of claim 1, wherein the prompting model is trained using a generative approach or a discriminative approach, and wherein the output of the prompting model predicts a likelihood of the user performing the task given a state of the user and a state of the user's environment.

9. The apparatus of claim 1, wherein the prompting model is trained using the discriminative approach comprising at least one of Logistic Regression, Random Forests, Extreme Gradient Boosting, and Deep Neural Networks.

10. A method for providing automated-prompting notifications for a user, the method comprising:
storing, via a non-transitory memory storage area, a schedule comprising a task to be performed by a user;
providing, via one or more processing devices, a first automated-prompting notification to the user to perform the task;
determining, via the one or more processing devices, that the user completed the task responsive to the first automated-prompting notification, wherein (a) a first state of the user and a first state of the user's environment are stored in association with the first automated-prompting notification, (b) the first state of the user, the first state of the user's environment, and the first automated-prompting notification are used to train a prompting model using machine learning, and (c) the prompting model outputs one or more automated-prompting notifications;
detecting, via the one or more processing devices, a first input indicative of a context of an environment of the user;
detecting, via the one or more processing devices, a first input indicative of a context of the user;
determining, via the one or more processing devices and based at least in part on the first input indicative of the context of the environment of the user and the first input indicative of the context of the user, a second state of the user and a second state of the user's environment;
determining, via the one or more processing devices and based at least in part on the second state of the user, the second state of the user's environment, and the prompting model, a second automated-prompting notification; and
providing, via the one or more processing devices, the second automated-prompting notification.

11. The method of claim 10, further comprising:
determining that the user completed the task responsive to the second automated-prompting notification; and
training the prompting model using machine learning based at least in part on the second state of the user, the second state of the user's environment, and the second automated-prompting notification.

12. The method of claim 11, further comprising:
detecting a second input indicative of a context of an environment of the user;
detecting a second input indicative of a context of the user; and
determining, based at least in part on the second input indicative of the context of the environment of the user and the second input indicative of the context of the user, a future state of the user and a future state of the user's environment; and
determining, based at least in part on the future state of the user and the future state of the user's environment, a prompting model.

13. The method of claim 10, wherein the first input indicative of the context of the environment of the user is selected from the group consisting of an activation state of a device, a proximity to an object, a proximity to a device, and a sound.

14. The method of claim 10, wherein the first input indicative of the context of the user is selected from the group consisting of a movement of the user, an activity of the user, an action of the user, a gesticulation of the user, a vocal expression of the user, a facial expression of the user, a schedule of the user, a visual perception of the user, an auditory perception of the user, a tactile perception of the user, a cognitive load of the user, a social restriction of the user, an interaction of the user with a device, and interaction of the user with other users, an interaction of the user with a medical dispenser, an interaction of the user with services, and an inferred intention of the user.

15. The method of claim 10, further comprising: controlling an output of a particular device by providing at least one control signal to the particular device.

16. The method of claim 15, wherein the prompting model is trained using the generative approach comprising at least one of Naïve Bayes, Linear Discriminant Analysis, Regularized Discriminant Analysis, Quadratic Discriminant Analysis, Gaussian Mixture Models, or Kernel Density Estimation.

17. The method of claim 10, wherein the prompting model is trained using a generative approach or a discriminative approach, and wherein the output of the prompting model predicts a likelihood of the user performing the task given a state of the user and a state of the user's environment.

18. The method of claim 10, wherein the prompting model is trained using the discriminative approach comprising at least one of Logistic Regression, Random Forests, Extreme Gradient Boosting, and Deep Neural Networks.

19. A computer program product comprising a non-transitory computer readable medium having computer program instructions stored therein, the computer program instructions when executed by a processor, cause the processor to:
store a schedule comprising a task to be performed by a user;
provide a first automated-prompting notification to the user to perform the task;
determine that the user completed the task responsive to the first automated-prompting notification, wherein (a) a first state of the user and a first state of the user's environment are stored in association with the first automated-prompting notification, (b) the first state of the user, the first state of the user's environment, and the first automated-prompting notification are used to train a prompting model using machine learning, and (c) the prompting model outputs one or more automated-prompting notifications;
detect a first input indicative of a context of an environment of the user;
detect a first input indicative of a context of the user;
determine, based at least in part on the first input indicative of the context of the environment of the user and the first input indicative of the context of the user, a second state of the user and a second state of the user's environment;
determine, based at least in part on the second state of the user, the second state of the user's environment, and the prompting model, a second automated-prompting notification; and
provide the second automated-prompting notification.

20. The computer program product of claim 19, wherein the computer program instructions further cause the processor to:
determine that the user completed the task responsive to the second automated-prompting notification; and
train the prompting model using machine learning based at least in part on the second state of the user, the second state of the user's environment, and the second automated-prompting notification.

21. The computer program product of claim 20, wherein the computer program instructions further cause the processor to:
detect a second input indicative of a context of an environment of the user;
detect a second input indicative of a context of the user; and
determine, based at least in part on the second input indicative of the context of the environment of the user and the second input indicative of the context of the user, a future state of the user and a future state of the user's environment; and
determine, based at least in part on the future state of the user and the future state of the user's environment, a prompting model.

22. The computer program product of claim 19, wherein the first input indicative of the context of the environment of the user is selected from the group consisting of an activation state of a device, a proximity to an object, a proximity to a device, and a sound.

23. The computer program product of claim 19, wherein the first input indicative of the context of the user is selected from the group consisting of a movement of the user, an activity of the user, an action of the user, a gesticulation of the user, a vocal expression of the user, a facial expression of the user, a schedule of the user, a visual perception of the user, an auditory perception of the user, a tactile perception of the user, a cognitive load of the user, a social restriction of the user, an interaction of the user with a device, and interaction of the user with other users, an interaction of the user with a medical dispenser, an interaction of the user with services, and an inferred intention of the user.

24. The computer program product of claim 19, wherein the computer program instructions further cause the processor to: control an output of a particular device by providing at least one control signal to the particular device.

25. The computer program product of claim 24, wherein the prompting model is trained using the generative approach comprising at least one of Naïve Bayes, Linear Discriminant Analysis, Regularized Discriminant Analysis, Quadratic Discriminant Analysis, Gaussian Mixture Models, or Kernel Density Estimation.

26. The computer program product of claim 19, wherein the prompting model is trained using a generative approach or a discriminative approach, and wherein the output of the prompting model predicts a likelihood of the user performing the task given a state of the user and a state of the user's environment.

27. The computer program product of claim 19, wherein the prompting model is trained using the discriminative approach comprising at least one of Logistic Regression, Random Forests, Extreme Gradient Boosting, and Deep Neural Networks.

* * * * *